(12) United States Patent
Krumpelmann et al.

(10) Patent No.: US 11,678,987 B2
(45) Date of Patent: Jun. 20, 2023

(54) COIL AND BARB ANCHORS FOR HEART VALVE REPAIR DEVICES

(71) Applicant: Boston Scientific Scimed, Inc., Maple Grove, MN (US)

(72) Inventors: Graham Krumpelmann, Stillwater, MN (US); Mathew L. Gilk, Brooklyn Park, MN (US); Joshua M. Inouye, Maple Grove, MN (US); James M. Anderson, Corcoran, MN (US); Timothy Hillukka, Rogers, MN (US); Kenny D. Bruner, Windsor, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 171 days.

(21) Appl. No.: 17/108,512

(22) Filed: Dec. 1, 2020

(65) Prior Publication Data
US 2021/0161664 A1 Jun. 3, 2021

Related U.S. Application Data

(60) Provisional application No. 62/942,802, filed on Dec. 3, 2019.

(51) Int. Cl.
*A61F 2/24* (2006.01)
(52) U.S. Cl.
CPC .......... *A61F 2/2466* (2013.01); *A61F 2/2445* (2013.01); *A61F 2220/0016* (2013.01); *A61F 2230/0091* (2013.01)
(58) Field of Classification Search
CPC ........ A61F 2/24; A61F 2/2445; A61F 2/2466; A61F 2/2487; A61F 2/2409
See application file for complete search history.

(56) References Cited

U.S. PATENT DOCUMENTS

| | | | |
|---|---|---|---|
| 4,989,617 | A | 2/1991 | Memberg et al. |
| 8,216,302 | B2 | 7/2012 | Wilson et al. |
| 8,506,623 | B2 | 8/2013 | Wilson et al. |
| 9,622,862 | B2 | 4/2017 | Lashinski et al. |
| 9,788,948 | B2 | 10/2017 | Gilmore et al. |
| 10,143,838 | B2 | 12/2018 | Grubac et al. |
| 10,548,731 | B2 | 2/2020 | Lashinski et al. |
| 2005/0107871 | A1 | 5/2005 | Realyvasquez et al. |
| 2009/0287304 | A1 | 11/2009 | Dahlgren et al. |

(Continued)

FOREIGN PATENT DOCUMENTS

WO 2009100242 A2 8/2009

OTHER PUBLICATIONS

International Search Report and Written Opinion for the International Patent Application No. PCT/US2020/062690, dated Apr. 1, 2021, 15 pages.

*Primary Examiner* — William H Matthews
(74) *Attorney, Agent, or Firm* — Seager, Tufte & Wickhem, LLP

(57) ABSTRACT

Anchoring assemblies that increase the surface area and/or amount of anchored tissue include a barb anchor, translatably disposed within the opening of an anchor housing, the barb anchor comprising a barb arm, the barb arm including a linear configuration wherein the barb arm is aligned with an axis of the opening and a deflected configuration wherein at least a portion the barb arm is deflected away from a central axis of the opening of the anchor housing.

20 Claims, 15 Drawing Sheets

(56) References Cited

U.S. PATENT DOCUMENTS

| | | |
|---|---|---|
| 2011/0082538 A1 | 4/2011 | Dahlgren et al. |
| 2011/0166649 A1* | 7/2011 | Gross .................... A61F 2/2466 |
| | | 623/2.36 |
| 2011/0172760 A1* | 7/2011 | Anderson .............. A61B 17/08 |
| | | 623/1.15 |
| 2017/0135816 A1 | 5/2017 | Lashinski et al. |
| 2018/0228610 A1 | 8/2018 | Lashinski et al. |

* cited by examiner

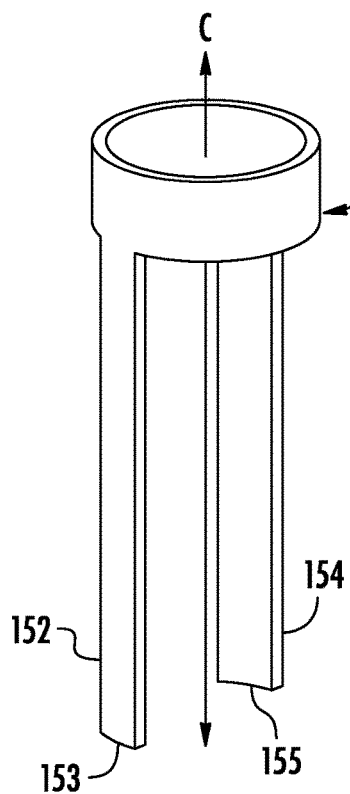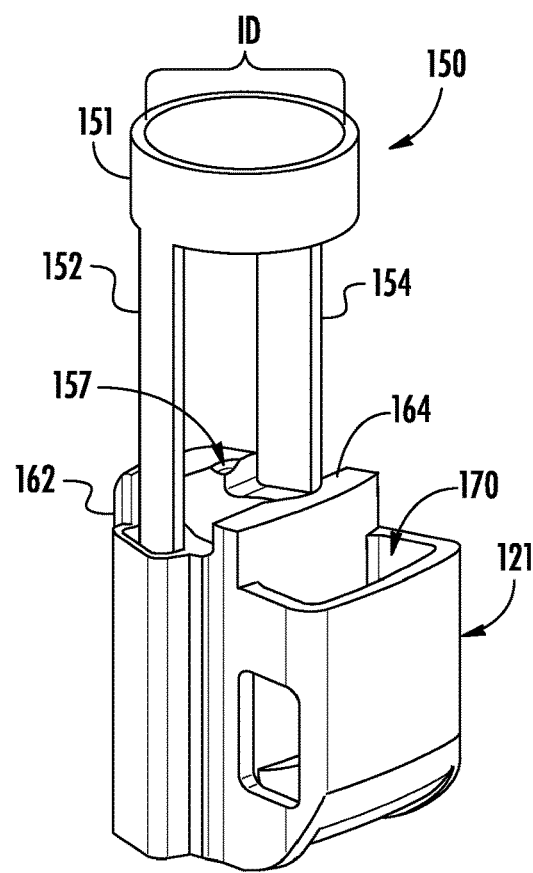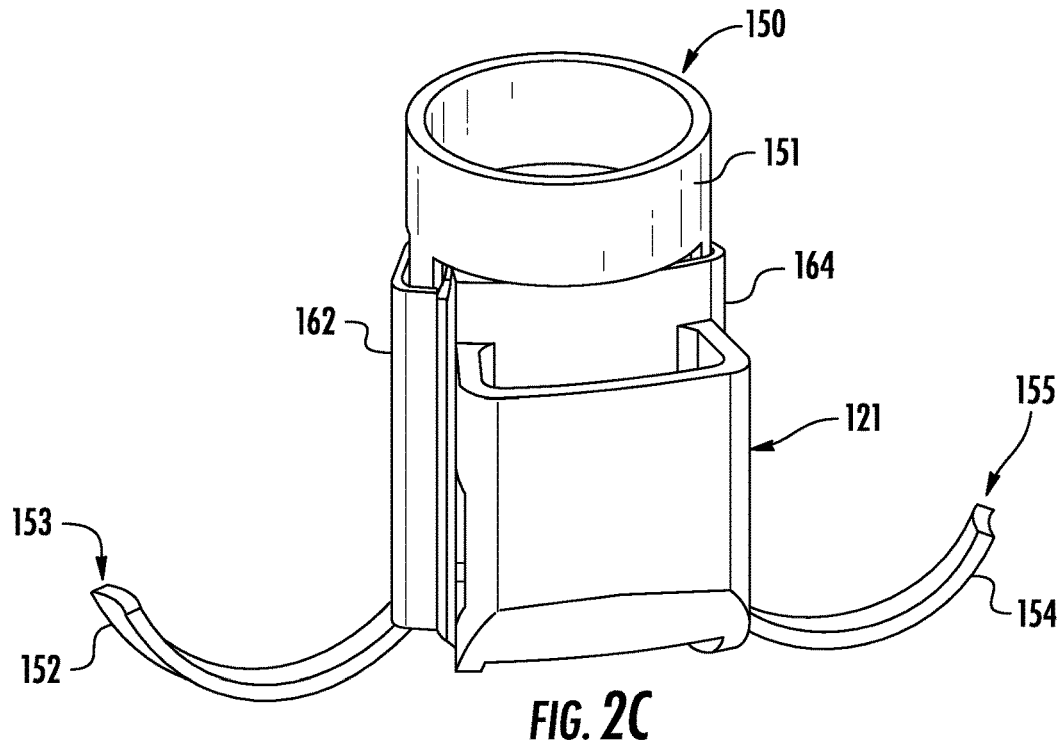
FIG. 2A
FIG. 2B
FIG. 2C

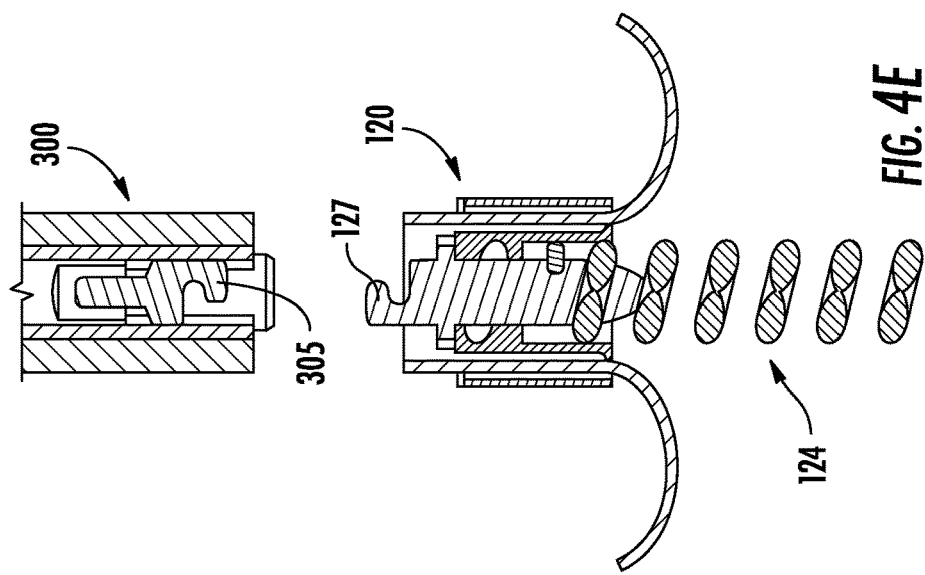
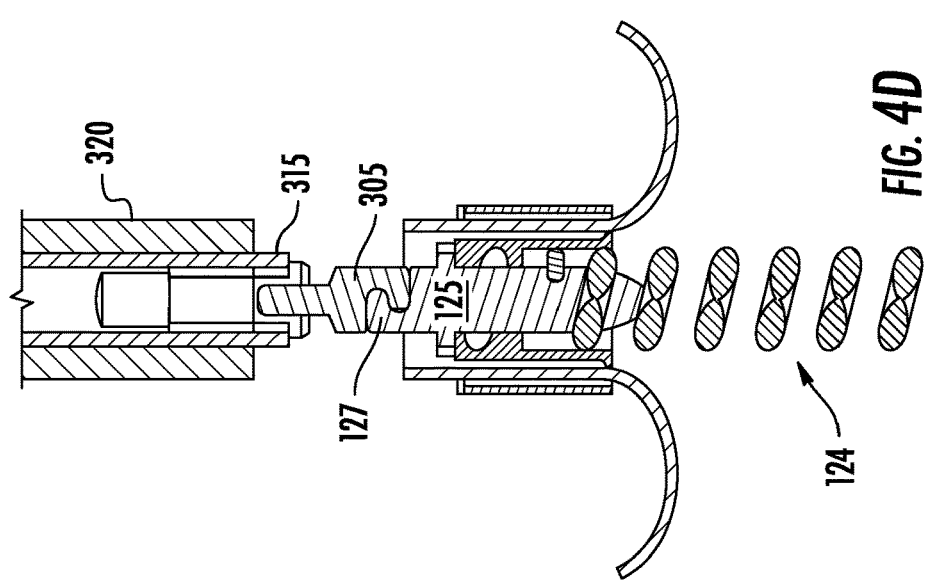
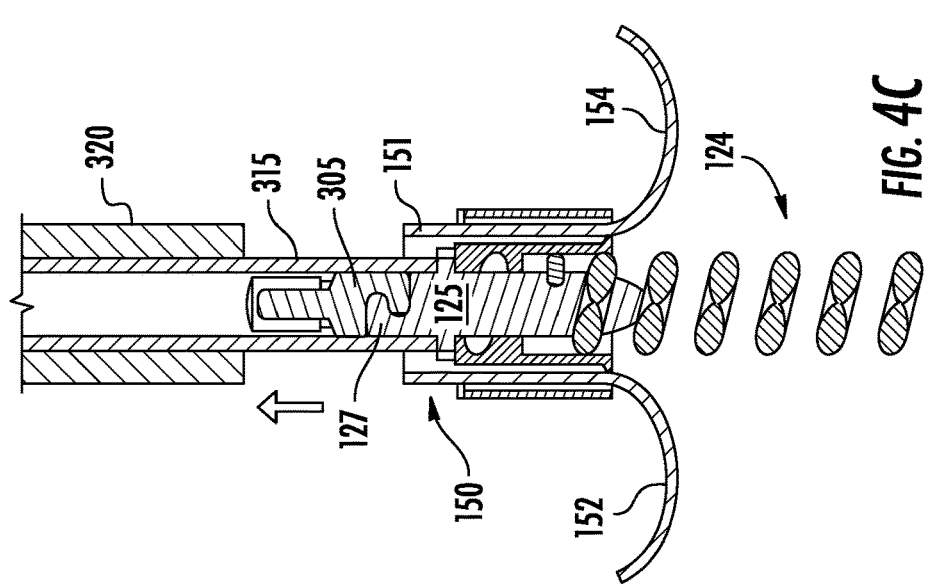
FIG. 4E
FIG. 4D
FIG. 4C

COIL AND BARB ANCHORS FOR HEART VALVE REPAIR DEVICES

CROSS-REFERENCE TO RELATED APPLICATIONS

The present application claims the benefit of priority under 35 U.S.C. § 119 to U.S. Provisional Patent Application 62/942,802, filed Dec. 3, 2019, which application is incorporated herein by reference in its entirety for all purposes.

FIELD

The technology disclosed herein generally relates to implantable coronary medical devices and more particularly to a customizable coronary implant.

BACKGROUND

Mitral insufficiency (MI) (also referred to as mitral regurgitation or mitral incompetence) is a form of heart disease where the mitral annulus dilates excessively and the valve leaflets no longer effectively close, or coapt, during systolic contraction. Regurgitation of blood occurs during ventricular contraction and cardiac output may decrease as a result. Surgical and endoluminal annuloplasty techniques have been introduced that aim to restore a mitral valve to its native configuration, for example by implanting an annuloplasty ring around a valve annulus. To ensure implant effectiveness, it is important that the integrity of the anchoring mechanism used to secure the implant to the valve annulus is able to accommodate the stresses and strains experienced by the implant as a result of chronic palpatory forces.

SUMMARY

The following disclosure describes non-limiting examples of some embodiments. The embodiments disclosed herein each have several aspects no single one of which is solely responsible for the disclosure's desirable attributes. For instance, other embodiments of the disclosed systems and methods may or may not include the features described herein. Moreover, disclosed advantages and benefits can apply only to certain embodiments and should not be used to limit the disclosure.

According to one aspect, an implant configured to be disposed about a cardiac valve may include a frame, an anchor housing, coupled to the frame and having an opening extending therethrough and a barb anchor, translatably disposed within the opening of the anchor housing. The barb anchor may include a barb arm, the barb arm may include a linear configuration where the barb arm is aligned with an axis of the opening and a deflected configuration where at least a portion the barb arm is configured to deflect away from a central axis of the opening of the anchor housing.

In various embodiments, the barb anchor may include a proximal end and a distal end, the proximal end may include a collar including a coupler for connecting the barb anchor to a driver, where the barb arm extends distally from the collar through the opening of the anchor housing. The barb arm may be one of a plurality of barb arms of the barb anchor. The plurality of barb arms may be configured to deflect away from the central axis of the opening of the anchor housing in different deflection directions. In some embodiments, at least two of the different deflection directions are opposing directions.

In various embodiments, the collar may be configured for mated engagement with a driver or the anchor housing, or both. At least one barb arm may be formed of a material that is biased towards the deflected configuration. In some embodiments, the barb anchor may include a neck at a proximal end and the collar may include a flange extending radially outward from the neck, the flange having a flange diameter that is smaller than a diameter of the opening. In some embodiments, the opening of the anchor housing may be one of a plurality of openings including a barb sleeve configured to retain the barb arm in the linear configuration for delivery of the implant to the cardiac valve, and a bore extending therethrough where the implant further may include a helical anchor translatably disposed within the bore. The helical anchor, the anchor housing or both may include a mechanism for translating the barb arm between the linear configuration and the deflected configuration.

According to another aspect, an implant delivery system includes a delivery catheter including a lumen extending therethrough, a drive tube extending through the lumen of the delivery catheter and having a distal end including a drive coupler and an implant, releasably coupled to the drive tube. The implant may include a frame, an anchor housing, coupled to the frame and having an opening extending therethrough and a barb anchor, translatably disposed within the opening of the anchor housing, the barb anchor including a barb arm having a linear configuration where the barb arm may be aligned with an axis of the opening and a deflected configuration where at least a portion the barb arm may be configured to deflect away from a central axis of the opening of the anchor housing. In various embodiments, the barb anchor may be releasably coupled to the drive coupler or the drive tube and the drive tube may be configured to drive the barb arm in the deflected configuration into tissue.

In some embodiments, the barb anchor may include a proximal end and a distal end, the proximal end including a collar having a coupler configured to connect the barb anchor to the drive coupler of the drive tube. In one embodiment, the barb arm may extend distally from the collar through the opening of the anchor housing in the linear configuration during delivery of the implant to a treatment site. The implant delivery system may further include a pusher tube, disposed about the drive tube. The opening of the anchor housing may be one of a plurality of openings of the anchor housing including a barb anchor sleeve configured to retain the barb arm in the linear configuration for delivery of the implant to a location proximate to a cardiac valve and a bore extending through the anchor housing. The implant further may include a helical anchor translatably disposed within the bore. In some embodiments, the collar may be releasably coupled to the pusher tube, and the drive tube may be configured to translate the helical anchor through the bore. In some embodiments, the pusher tube may be configured to drive the barb arm through the barb anchor sleeve and the pusher tube and drive tube may be independently controlled. According to one embodiment, the implant delivery system further may include a barrel, coupled to a proximal end of the opening, the barrel configured to retain the barb anchor in the linear configuration during delivery of the implant to a treatment site.

In various embodiments, the barb arm may be one of a plurality of barb arms of the barb anchor. The barb arms may be configured to deflect away from the central axis of the opening of the anchor housing in different deflection directions, where at least two of the different deflection directions are opposing directions.

According to another aspect, a method of deploying an implant to a cardiac valve may include the steps of forwarding a delivery catheter carrying an implant at a distal end to a treatment site proximate the cardiac valve, the implant including a frame including an anchor housing having at least one opening for translatably supporting a plurality of anchors including a barb anchor and a helical anchor and independently driving the helical anchor and the barb anchor into tissue, where the helical anchor and barb anchor each enter tissue at different angles relative to a central axis defined by the at least one opening.

In one embodiment, the opening of the anchor housing may be one of a plurality of openings including a barb anchor sleeve configured to retain the barb anchor in a linear configuration for delivery of the implant to the cardiac valve and a bore extending through the anchor housing configured for translation of the helical anchor. The step of independently driving may include the steps of driving the helical anchor through the bore of the anchor housing using a drive tube coupled to the helical anchor and driving the barb anchor through the barb anchor sleeve using a pusher tube, disposed about the drive tube, the barb anchor transforming to a deflected configuration when released from the barb anchor sleeve.

In an embodiment where the barb anchor is disposed about the helical anchor and includes a linear configuration where at least one barb arm of the barb anchor is aligned with an axis of the opening and a deflected configuration where at least a portion the barb arm is configured to deflect away from a central axis of the opening of the anchor housing, the method may include the steps of distally translating the helical anchor through the opening of the anchor housing by actuating a drive tube coupled to the helical anchor, engaging a tooth of the helical anchor with a slot of the anchor housing to limit distal translation of the helical anchor through the anchor housing and actuating the drive tube with the tooth of the helical anchor housing engaged with the slot of the anchor housing to translate the barb anchor from the linear configuration to the deflected configuration.

In an embodiment where the barb anchor is disposed about the helical anchor and includes a linear configuration where at least one barb arm of the barb anchor is aligned with an axis of the opening and a deflected configuration where at least a portion the barb arm may be configured to deflect away from a central axis of the opening of the anchor housing, and the helical anchor includes a deflection feature disposed thereon, the method may include the steps of distally translating the helical anchor through the opening of the anchor housing by actuating a drive tube coupled to the helical anchor and distally translating the barb anchor over the helical anchor towards the deflection feature of the helical anchor until the barb anchor may be deflected away from the helical anchor by the deflection feature.

With such an arrangement, various embodiments of anchoring assemblies are provided that increase the distribution surface area of load forces at a target treatment site to thereby improve the retention and efficacy of an implant.

BRIEF DESCRIPTION OF THE DRAWINGS

The foregoing and other features of the present disclosure will become more fully apparent from the following description and appended claims, taken in conjunction with the accompanying drawings. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawings, can be arranged, substituted, combined, and designed in a wide variety of different configurations, all of which are explicitly contemplated and made part of this disclosure.

FIGS. 2A-2C illustrate one embodiment of a barb anchor that may be included in the multi-anchor implant of FIG. 1;

FIGS. 4A-4E illustrate embodiments of a multi-anchor assembly provided to illustrate a method for independently driving the anchors into tissue;

DETAILED DESCRIPTION

Heart disease impedes patient cardiac output, which reduces patient quality of life and lifespan. When heart valves fail to property coapt, or close, during their cardiac cycle, blood may leak backwards into the atrium each time the left ventricle contracts. Various procedures have been implemented to overcome valve insufficiency. These procedures include methods for restoring structural integrity to the valve annulus (a fibrous ring partially surrounding a heart valve) and/or repairing flailing leaflets resulting from stretched or torn chordae. Many of these methods involve anchoring an implant or other object to heart tissue. For example, annuloplasty may involve securing an implant including a ring or frame around a valve annulus using anchors. Such implants are subject to chronic stresses and strains from the palpatory motion of the heart muscle and thus it is important that the implant is securely anchored to cardiac tissue.

The present disclosure describes various embodiments of anchoring systems which improve retention of a cardiac implant by distributing anchoring forces over a greater surface area of the cardiac tissue. In one embodiment, the forces may be distributed using barb anchors which curve or otherwise deflect away from a central anchoring axis as they are deployed, thereby increasing the resistive surface area of the anchor. For example, the barb anchors may include one or more barb arms having distal ends that deflect away from a central anchoring axis, either due to the resilient nature of the barb arm, through mechanical manipulation of the barb arm, or a combination thereof. In some embodiments, the barb arms may be used together with helical anchors which secure tissue along the central anchoring axis, thereby increasing the surface area and security of implant affixation.

Various embodiments of anchoring solutions that use barb anchors in various forms are described below. Although embodiments of the present disclosure may be described with specific reference to mitral valves, an anchor housing such as that disclosed herein that provides customizable depth anchoring may be readily adapted to facilitate reconstruction of any valve annulus, for example including a tricuspid valve annulus and/or may similarly benefit any other dilatation, valve incompetency, valve leakage and other similar heart failure conditions which involve anchoring a component to heart tissue.

As used herein, the term "distal" refers to the end farthest away from the medical professional when introducing a medical device into a patient, while the term "proximal" refers to the end closest to the medical professional when introducing a medical device into a patient. A central axis means, with respect to an opening, a line that bisects a center point of the opening, extending longitudinally along the length of the opening when the opening comprises, for example, a sleeve or a bore.

Figure 1:
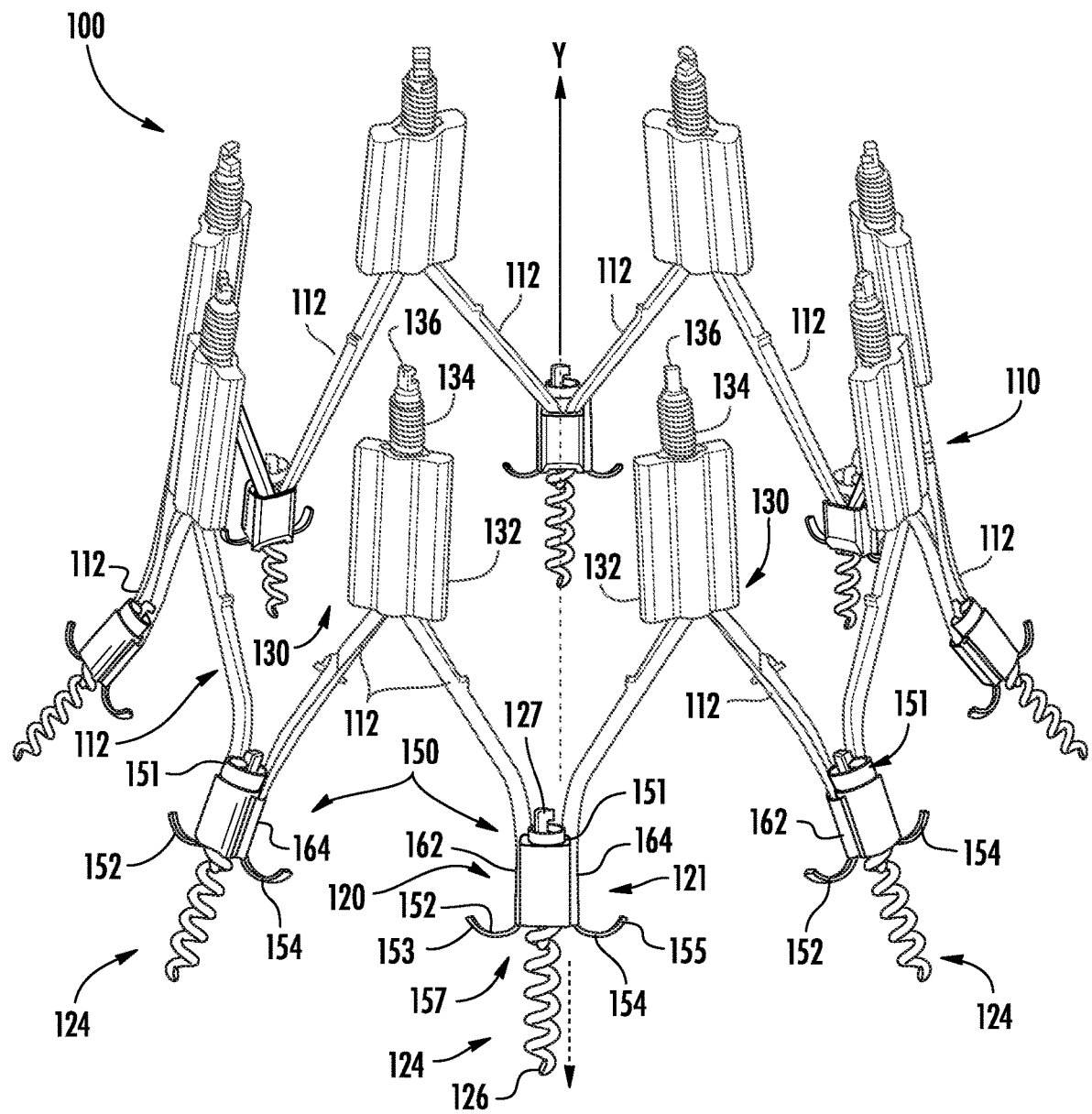
FIG. 1 illustrates one embodiment of a multi-anchor implant as disclosed herein.

FIG. 1 illustrates an implant 100 comprising a frame 110 that may be disposed about a heart valve or other cardiac feature. For purposes of clarity not all of the components of the implant are numbered. In one embodiment, the frame 110 may extend circumferentially around and partially axially along a central frame axis Y extending proximally-distally through a center point of the frame. The frame 110 may be generally symmetric with respect to the central frame axis Y although it need not be symmetric. The frame 110 may form a generally tubular shape, where herein "tubular" includes circular as well as other rounded or otherwise closed shapes. The frame 110 may be configured to change shape, size and/or configuration. For example, the frame 110 may assume various shapes, sizes, configurations etc. during different phases of deployment such as during pre-delivery, delivery, tissue engagement and cinching.

According to one embodiment, the frame 110 may be formed from one or more struts 112 that may form all or part of the frame 110, where the struts 112 may include elongated structural members formed of a metal alloy, a shape memory material, such as an alloy of nickel titanium or other metals, metal alloys, plastics, polymers, composites, other suitable materials, or combinations thereof. In FIG. 1 sixteen struts 112 are shown although it is appreciated that in some embodiments, there may be fewer or more than sixteen struts.

In one embodiment, the struts 112 of the frame 110 may be formed from the same, monolithic piece of material. Thus, reference to struts 112 may refer to different portions of the same, extensive component. Alternatively, reference to struts 112 may refer to components that are formed separately and attached permanently together, for example by welding or other methods. In some embodiments, the struts 112 may be separate components that are detachably coupled together to form proximal and distal apices. For example, the struts 112 are shown joined at their proximal apex by actuator 130 and at their distal apex by anchoring assemblies 120.

In some embodiments, the terms "apex," apices," and the like may be used interchangeably with terms "crown," "crowns," and the like, as used herein and as used in any reference incorporated by reference herein, unless otherwise stated. In one embodiment, an 'apex' may include a proximal or distal portion of the frame.

In one embodiment, the actuator 130 includes an actuator shaft 134 that is rotatably carried by the proximal end of the frame 110, for example, a head of the actuator shaft 134 may be carried by a window or other opening (not shown) at the proximal apex of the frame 110. The actuator shaft 134 may include a drive coupler 136 at the proximal end. The actuator 130 may further include an actuator collar 132 having internal features configured to interact with the features of the actuator shaft 134 such that rotation of the actuator shaft 134 by an actuator drive tube coupled to the drive coupler 136 axially translates the actuator collar 132 over the actuator shaft 134 and over struts 112. In some embodiments, "axial" as applied to axial movement or restraint of the actuator collar includes directions that are at least partially in the proximal or distal direction and that are parallel or generally parallel to a central axis extending through (proximally—distally) the frame, such as at least partially in along axis Y. As shown in FIG. 1, struts 112 extend away from the proximal apex in opposing directions. Distal advancement of the actuator collar 132 over struts 112 pulls the struts together within the actuator collar 132, thereby 'cinching' the frame and reducing the distance between anchoring assemblies 120 to reshape heart tissue anatomy, for example to restore a valve to its native configuration. In one embodiment, each actuator collar 132 may be independently actuated in accordance with the reshaping objective for the associated anchor pair.

Although FIG. 1 illustrates an implant that uses actuators 130 to cinch the frame 110, it will be readily appreciated that the anchoring systems described herein may be used with any cardiac implant device that seeks to improve anchoring integrity by increasing anchoring surface area. For example, implants that use a lasso mechanism to draw together struts, or that use ratchet type collars driven over strut apices to reduce spacing between distal apices are considered within the scope of this disclosure. Further, it is appreciated that the anchoring systems disclosed herein are equally beneficial for use with implants which do not use cinching mechanisms. Accordingly, the present disclosure is not limited by the particular implant disclosed herein.

The implant further includes anchoring assemblies 120. Each anchoring assembly 120 is shown to include an anchor housing 121, a barb anchor 150, and a helical anchor 124. The barb anchor 150 is shown in the embodiment of FIG. 1 to comprise a collar 151 and a pair barb arms 152, 154. The anchor 124 includes a proximal drive coupler 127 and a helical coil 126, which may have a sharpened distal tip.

The anchor housing 121 may include one or more openings for supporting the anchors. For example, anchor housing 121 is shown to include barb arm sleeves 162, 164 and a bore 157. In one embodiment, to deploy the anchors, the barb arms 152, 154 may be advanced through the respective barb arm sleeves 162, 164, and the helical anchor 124 may be advanced through the bore 157 to engage tissue proximate to a cardiac valve, for example tissue of a mitral valve annulus.

In one embodiment, the barb arms 152, 154 may be formed from a shape memory alloy (SMA) or similar materials with the ability to recover a pre-defined configuration. Such materials include, but are not limited to, Nickel Titanium, Graphene, Nitinol, copper-aluminum-nickel, and the like. In one embodiment, the barb arms 152, 154 may be biased towards the pre-defined configuration, where in the biased configuration, at least a portion of the barb arm is deflected away from a central axis extending through the barb sleeve. For example, in FIG. 1, the barb arms 152, 154 are shown to be biased in a curved configuration, wherein the distal ends 153, 155 of the barb arms 152, 154 deflect away from the central axis extending through their respective barb arm sleeves 162, 164. With such an arrangement, as the barb arms 152, 154 are driven into tissue, the surface area of anchored tissue spans between the distal tips 153, 155 of the anchoring assembly 120, improving retention of the frame 110.

FIGS. 2A-2C illustrate one embodiment of the barb anchor 150 in more detail. In FIG. 2A, the barb anchor 150 is shown to include a collar 151 including a plurality of barb arms 152, 154 extending distally therefrom. In one embodiment, the barb anchor 150 may be formed from a nitinol tube having a 0.1" outer diameter (OD), and a thickness of 0.010", which may be laser cut to form the collar 151 and barb arms 152, 154. Following cutting, the barb arms 152, 154 may be processed to retain their biased, deflected configuration, for example using conventional shaped memory methods. In one embodiment, each barb arm 152, 154 may have a length of at least about 6 mm (millimeters) and at most about 12 mm, for example, including increments of 0.1 mm therebetween, and the distal end 153, 155 may be formed to deflect at least about 10 degrees and at most about 180 degrees, including increments of 0.5 degrees therebetween, away from the central axis defined by the barb arm sleeve. The deflected configuration of the barb arms enables the barb arms to leverage the resistive force of annulus tissue to secure the anchor housing to the tissue. The distal ends 153, 155 may be beveled or otherwise sharpened to enable the barb arms to cut through tissue. FIG. 2A illustrates the barb anchor 150 in a linear configuration, e.g., wherein the distally extending barb arms 152, 154 are generally parallel to a central axis "C" of the collar 151.

In some embodiments, the length and/or deflection configuration of anchors may vary, or be tuned, to control the depth and/or extend of the barb arm as it is forwarded into tissue. Thus, implants may be provided including both barb anchors that embed less deeply across smaller spans (for example, which may be used at locations near the valve, such as the commissure, having less tissue depth) as well as barb anchors having a deeper, broader, reach (for example, which may be used at valve locations having more tissue and experiencing greater palpatory stresses and strains). Thus, although the drawings illustrate deployment of barb anchors having a uniform configuration, the present disclosure is not so limited.

Figure 2D:
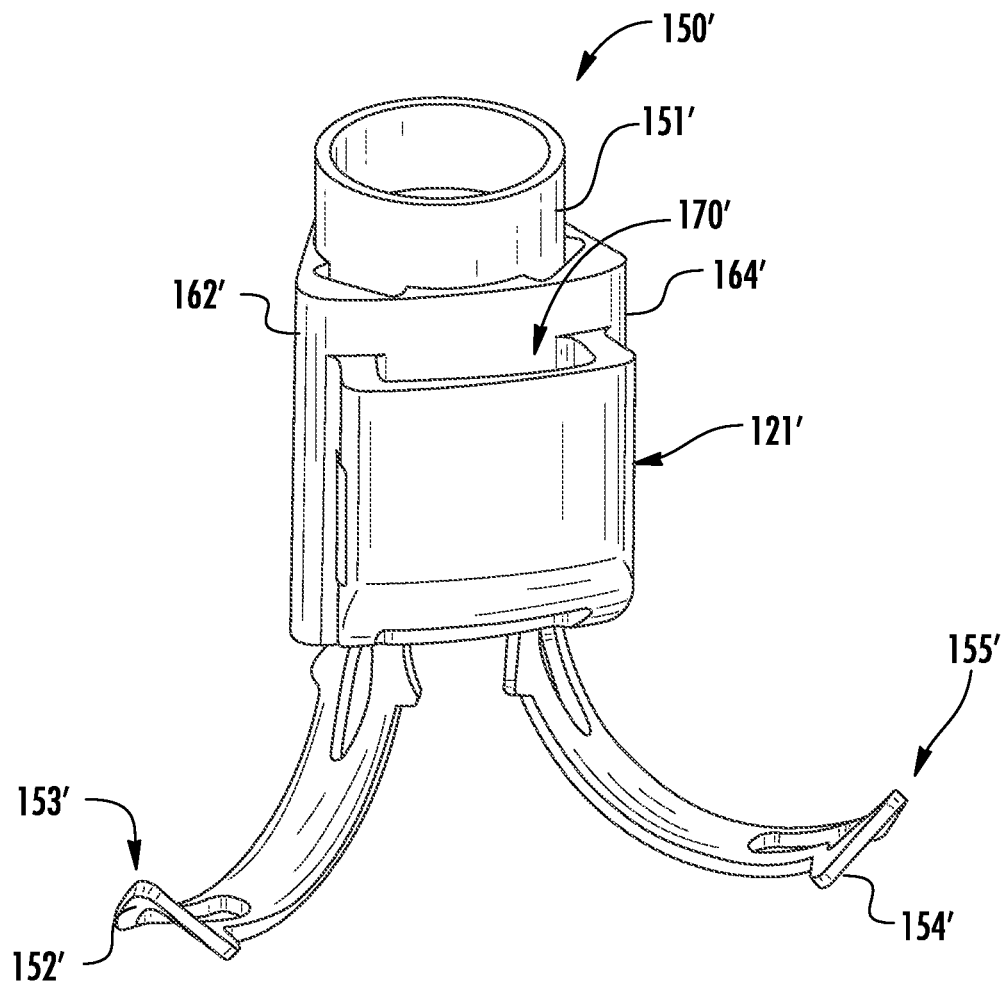
FIG. 2D illustrates an alternative embodiment of a barb anchor that may be included in the multi-anchor implant of FIG. 1.
Figures 2E, 2F:
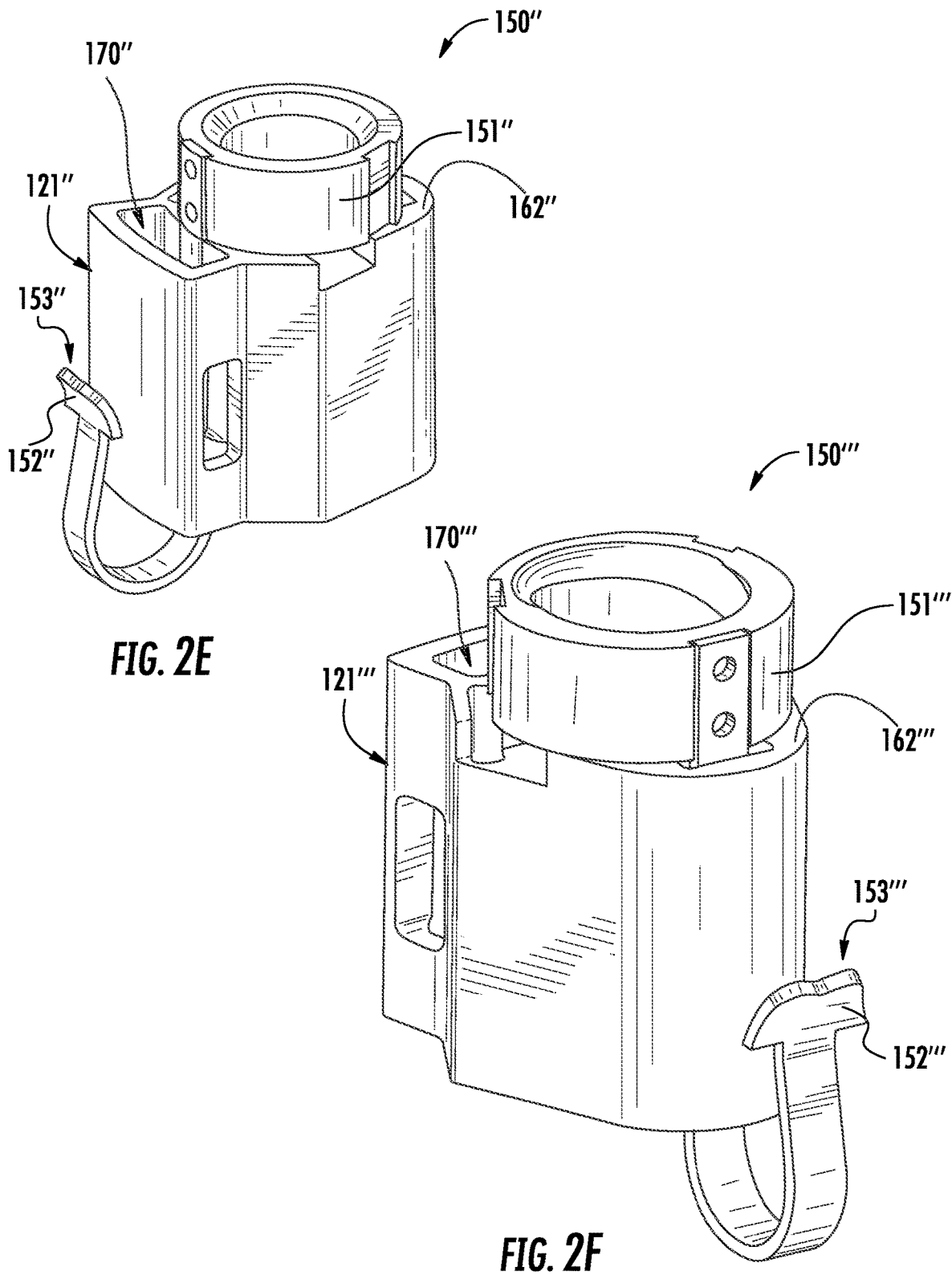
FIG. 2E illustrates another alternative embodiment of a barb anchor that may be included in the multi-anchor implant of FIG. 1.
FIG. 2F illustrates another alternative embodiment of a barb anchor that may be included in the multi-anchor implant of FIG. 1.

In one embodiment, the barb arms 152, 154 of barb anchor 150 may be retained in the linear configuration by the barb arm sleeves 162, 164 of the anchor housing 121 as shown in FIG. 2B. In one embodiment, the anchor housing 121 may include a plurality of openings, including barb arm sleeves 162, 164 configured to slidably accept the barb arms 152, 154 as the barb anchor 150 is slid into the anchor housing 121. In general, the position and number of the barb arm sleeves are matched in configuration to the position and number of barb arms of the barb anchor. It will be appreciated that although the barb arm sleeves 162, 164 and the corresponding barb arms 152, 154 are illustrated in FIG. 2C as spaced apart at substantially opposite sides of the anchor housing 121 (e.g., approximately 180 degrees apart around the collar 151), other relative spacings are considered to be within the scope of this disclosure. For instance, the barb arm sleeves 162', 164' and the corresponding barb arms 152', 154' of an alternative barb anchor 150', as illustrated in FIG. 2D, may be positioned closer together than 180 degrees about the perimeter of the anchor housing 121' and collar 151'. Moreover, although two barb arm sleeves 162, 164 are shown positioned to slidably accept and retain two barb arms 152, 154, other barb anchor embodiments that include one, three, or more barb arms may be used together with anchor housings including one, three, or more openings and therefore are considered to be within the scope of this disclosure. As illustrated in FIG. 2E, another alternative barb anchor 150" may include a single barb arm 152" extending from a collar 151" distally along the anchor housing 121" and along the frame slot 170". It is noted that in the examples illustrated in FIGS. 2D and 2E, the barbs are on the exterior side of the anchor housing 121', 121" and substantially on the same side as the frame slot 170', 170" (and would be positioned around the outer perimeter of a frame 110 on which the anchor housing 121', 121" is provided). Alternatively, as illustrated in the embodiment of FIG. 2F, a barb arm 152''' (or more than one barb arm, such as the two barb arms of FIG. 2D) may be provided on the interior side of an anchor housing 121''' (e.g., opposite the side along which the frame slot 170''' is positioned), extending distally from a collar 151''' and through an associated sleeve 162''' in an anchor housing 121''' of the barb anchor 150'''. The barb arm 152''' thus would extend along the inner perimeter of a frame 110 on which the anchor housing 121''' may be provided.

It is noted that the distal ends 153', 155', 153", 153''' of the barb arms 152', 154', 152", 152''', respectively, may be configured as in the other embodiments described herein, or may be somewhat more pointed, as illustrated, to facilitate entry into the annulus tissue. A single pointed end (as in FIG. 2D) or a double-pointed configuration (as illustrated in FIG. 2E and FIG. 2F) may be provided on any of the barb arms described herein.

In some embodiments, the anchor housing 121 may include additional openings for accepting additional components of the implant. For example, the anchor housing 121 is shown to include a bore 157 which may be configured to support a helical anchor as described with regard to FIG. 1. In one embodiment, an inner diameter (ID) of the collar 151 is selected to be larger than a diameter of the bore 157, to reduce the potential of interference between the barb anchor 150 and any anchor forwarded through the bore 157. The embodiment of the anchor housing 121 of FIG. 2B is further shown to include a frame slot 170 which may be used to couple the anchor housing 121 to a distal apex of the frame 110 (FIG. 1). For example, the struts of the distal end of the frame may be welded, snap fit, or otherwise securely coupled within the frame slot 170 of the anchor housing 121.

FIG. 2C illustrates the barb anchor 150 following advancement of the barb arms 152, 154 through the barb arm sleeves 162, 164 of the anchor housing 121. As will be discussed in more detail below, the barb arms 152, 154 may be advanced through the barb arms sleeves 162, 164 by distal advancement of the collar 151. In FIG. 2C, the barb arms 152, 154 are shown to have returned to their biased, deflected configuration, wherein the distal ends 153, 155 are deflected away from a longitudinal axis of the collar 151, and concomitantly the central axis of the barb arm sleeves 162, 164. As a result, the total surface area of anchored tissue spans the length between the distal tips 153, 155 of the barb arms, increasing the span of anchored tissue and improving anchoring integrity.

Figure 3A:
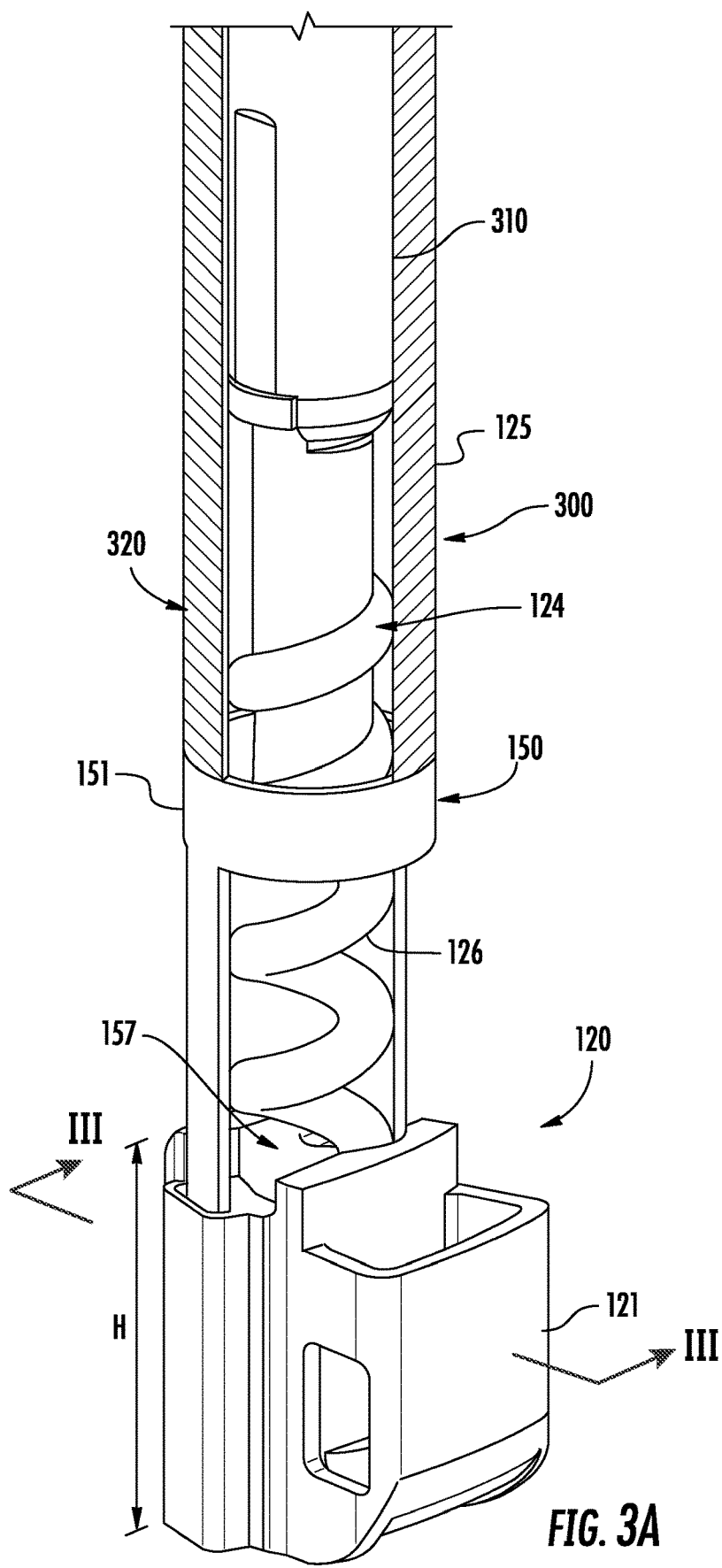
FIGS. 3A-3C illustrate examples of embodiments of a multi-anchor assembly coupled to a drive tube.

FIG. 3A illustrates one embodiment of an anchoring assembly 120 coupled to an anchor drive mechanism 300. The anchor drive mechanism 300 is configured to drive the helical anchor 124 as well as the barb anchor 150 into tissue. The helical anchor 124 is shown to include a distal helical coil 126 coupled to a proximal shaft 125. A coupler (not shown) is disposed at the proximal end of the proximal shaft 125 and is matingly coupled to a drive coupler (not shown) of a drive shaft 310. In one embodiment, rotation of the drive shaft 310 axially translates the anchor 124 through the bore 157 of the anchor housing 121.

Figure 3B:
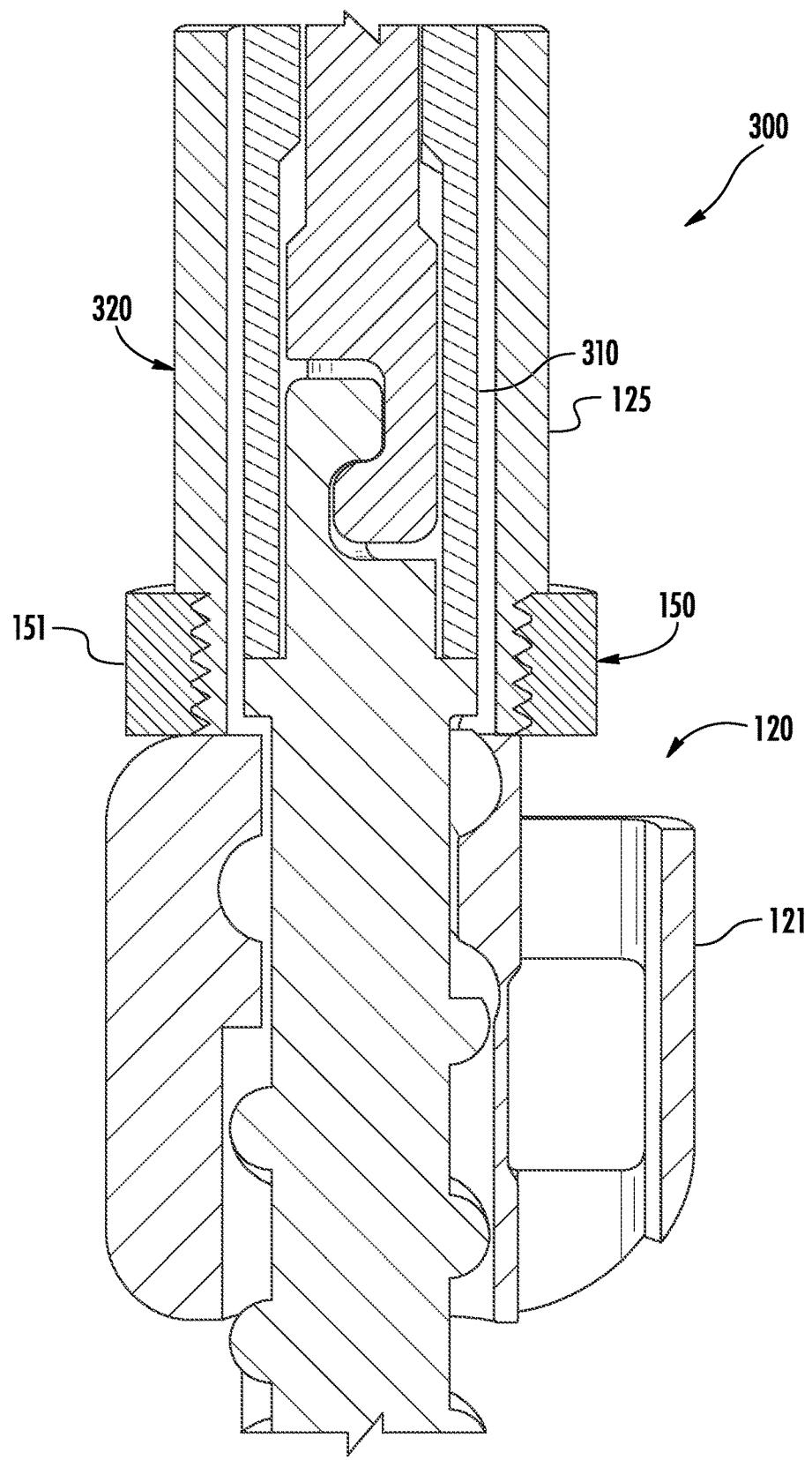
Figure 3C:
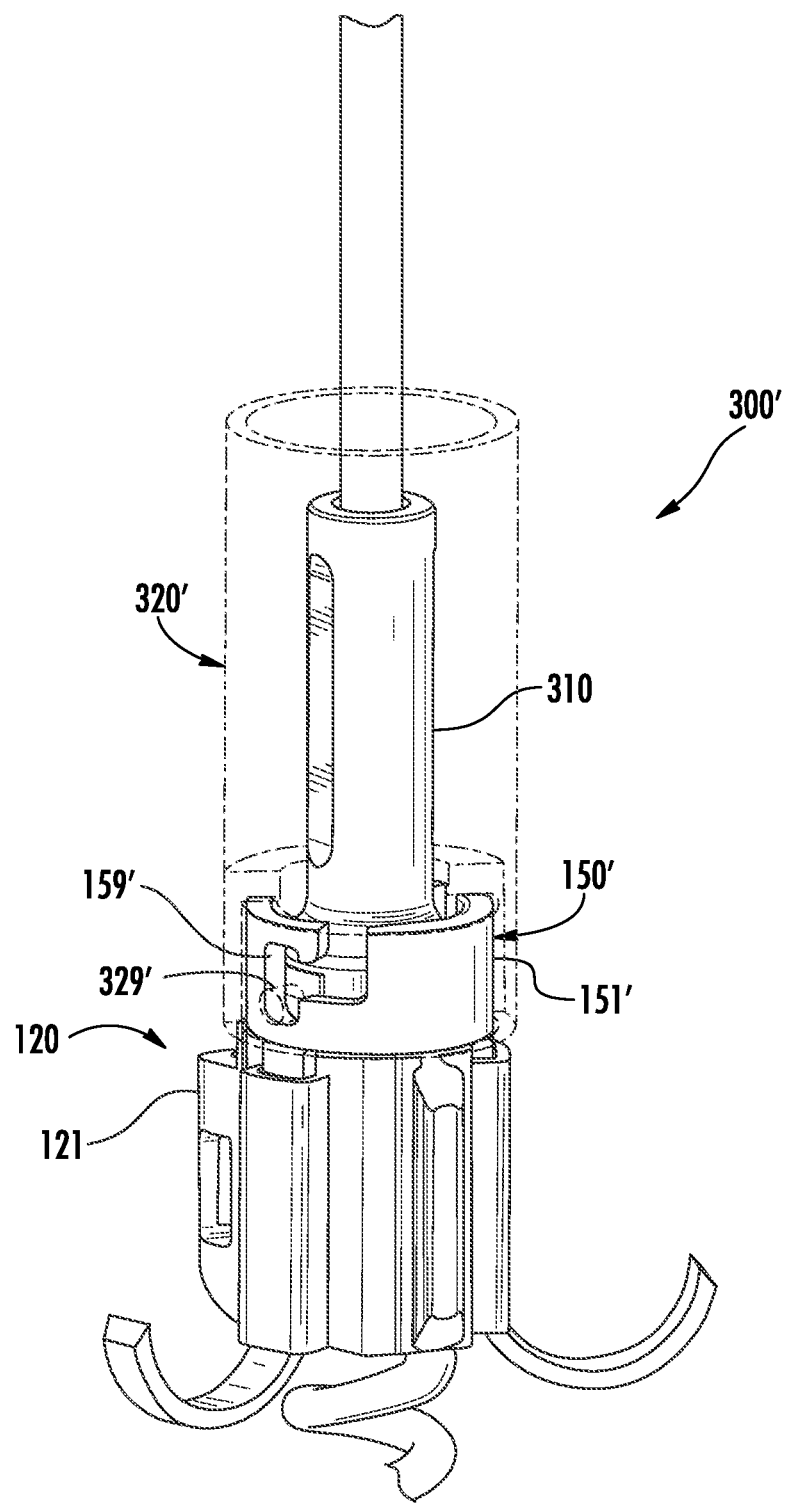

The anchor drive mechanism 300 further includes a pusher tube 320, disposed about the drive shaft 310. The pusher tube 320, in one embodiment, is coupled to the collar 151 of the barb anchor 150. For example, the pusher tube 320 may include one or more threads, teeth, nubs, or other features which interact with one or more threads, slots, divots, or complementary features of the collar 151 to secure the pusher tube 320 to the collar 151, enabling the collar 151 to be translated distally and/or proximally in coordination with distal and/or proximal actuation of the pusher tube 320. For example, the distal end of the pusher tube 320 may threadedly engage the collar 151 as illustrated in FIG. 3B (showing a cross-section along line III-III of FIG. 3A). Alternatively, as illustrated in FIG. 3C, an anchor drive mechanism may be substantially similar to the anchor drive mechanism illustrated in FIG. 3A (with similar parts labeled with similar reference numbers), other than the coupling of the pusher tube 320' to the collar 151'. As illustrated, the pusher tube 320' and collar 151' of the anchor drive mechanism 300' of FIG. 3C may be coupled with a connection such as a pin and slot connection (e.g., a Luer lock type connection), the slot 159' having axial and radial components such that the pin 329' is engaged or released by rotational and axial movement. In FIGS. 3A and 3B, the pusher tube 320 is shown in cross section, whereas in FIG. 3C the pusher tube 320' is shown in phantom. In some embodiments, the pusher tube 320 may be a unitary tube; in alternate embodiments, the pusher tube 320 may be comprised of one or more arms, with openings disposed therebetween. Accordingly, the disclosure is not limited to use of a unitary pusher tube.

In some embodiments, the helical anchor 124, barb anchor 150, and anchor housing 121 may be made of a suitable biocompatible metal alloy such as stainless steel, cobalt chromium, platinum iridium, nickel titanium, other suitable materials, or combinations thereof. The helical anchor 124 and barb anchor 150 may be at least about 10 mm and at most about 15 mm, including increments of 0.1 mm therebetween, in total axial length. In some embodiments, the anchors 124, 150 may be shorter or longer than about 10 to 15 mm (including increments of 0.1 mm therebetween) in total axial length. In various embodiments, the total axial lengths of the helical anchor and one or both barb arms may differ. By "total" axial length it is meant the axial length of the anchors from the end of the distal penetrating tips to the opposing proximal anchor head or collar. The helical coil 126 of the anchor 124, and the barb arms 152, 154 may be at least about 6 mm and at most about 12 mm, including increments of 0.1 mm therebetween, in axial length. In some embodiments, the helical coil or barb arms may be shorter or longer than about 6 mm to 12 mm in axial length, including increments of 0.1 mm therebetween. The proximal head of the helical anchor 124 (including proximal anchor coupler (shown, for example, in FIGS. 3B and 3C) and shaft 125), or collar 151 and/or other non-helical proximal portions of the anchors may be at least about 3 and at most about 4 mm, including increments of 0.01 mm therebetween, in axial length. In some embodiments, the proximal anchor head, collar, and/or other non-helical portions may be shorter or longer than 3 mm to 4 mm in axial length.

In some embodiments, the helical coil 126 and/or the barb arms 152, 154 may be capable of extending at least about 4 mm and at most about 7 mm, including increments of 0.1 mm therebetween, axially beyond the distal surface of the anchor housing 121. In some embodiments, the anchor housing 121 may have a height H at least about 2.5 mm and at most about 5 mm, including increments of 0.1 mm therebetween.

Figure 4B:
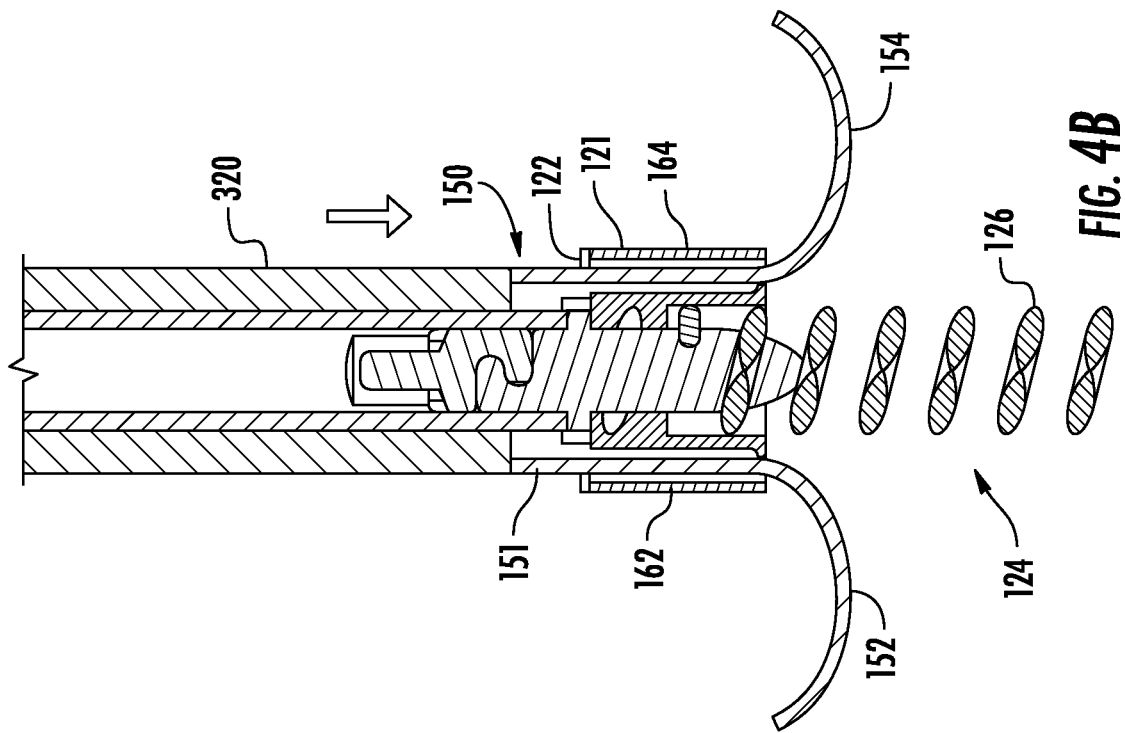
Figure 4A:
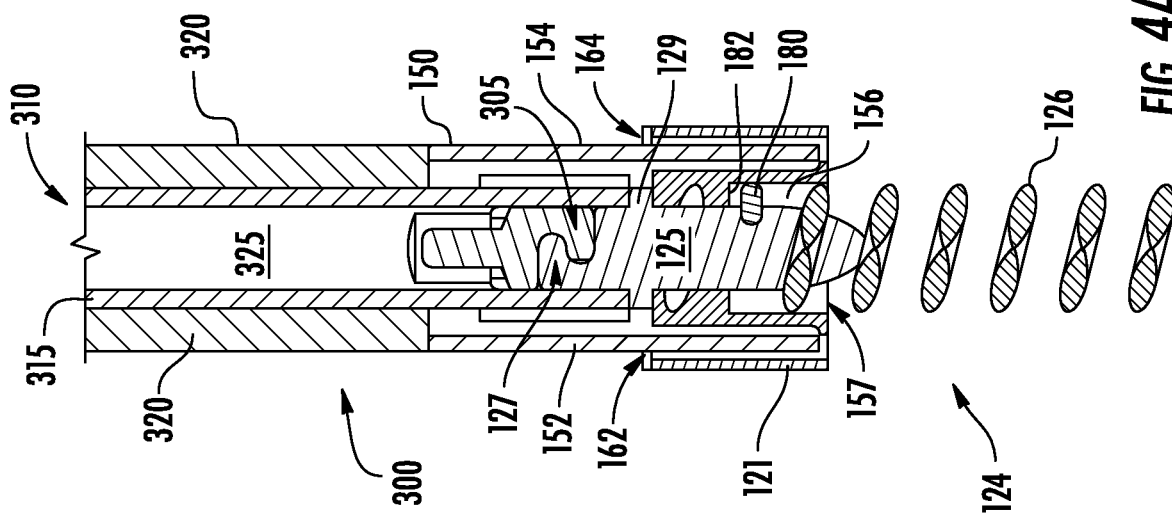

FIGS. 4A-4E illustrate, in partial cross-sectional view, the deployment of a barb anchor 150 and a helical anchor 124, for example using the driver assembly 300 of FIG. 3A. In FIG. 4A, the drive assembly 300 is shown to include a drive shaft 310 terminated at its distal end by a drive coupler 305. The drive shaft 310 is translatably disposed within a drive sheath 315. Disposed about the drive sheath is a pusher tube 320. In FIG. 4A, a helical coil 126 of an anchor 124 has been advanced into tissue, for example by rotation of the shaft 325 and resulting interaction between the drive coupler 305 and the coupler 127 at the proximal end of the shaft 125 of the anchor 124. In one embodiment, the anchor 124 is rotated until a flange 129, extending radially outward from the shaft 125 of the anchor 124 contacts a surface of the anchor housing 121, impeding further distal translation of the anchor 124 into tissue. In one embodiment, the anchor housing 121 advantageously includes a ledge 182, disposed within the anchor housing such that a most proximal turn 180 of the helical coil 126 is below the ledge 182 when the flange 129 contacts the surface of the anchor housing 121. As a result, the interaction between the ledge 182 and the turn 180 of the helical coil 126 helps to retain the anchor 124 within the anchor housing.

In addition, according to one embodiment, the bore 157 of the anchor housing includes an unthreaded portion 156. The unthreaded portion 156 provides a 'free spin' space for the anchor 124. When the anchor 124 has been advanced distally until the flange 129 contacts the outer surface of the anchor housing 121 and further distal translation of the anchor is impeded, the free space 156 permits the anchor 124 to continue to rotate freely, drawing tissue up towards the anchor housing 121 to improve affixation between the anchor housing 121 and the tissue.

According to one embodiment, while the helical anchor 124 is being advanced into tissue, the pusher tube 320 is maintained in a relatively proximal position, retaining the barb arms 152, 154 of the barb anchor 150 within the barb arm sleeves 162, 164 in a linear configuration.

Referring now to FIG. 4B, once the helical anchor 124 is deployed, the pusher tube 320 is distally advanced, pushing the barb arms 152, 154 through the barb arm sleeves 162, 164, for example by action of the pusher tube 320 upon the collar 151 of the barb anchor 150, until further advancement of the barb anchor 150 is impeded by contact between the collar 151 and the proximal surface 122 of the anchor housing 121. As the barb arms 152, 154 are released from the sleeves 162, 164, they assume their biased, deflected configuration as shown in FIG. 4B.

Once the helical anchor 124 and the barb arms 152, 154 have been deployed, the barb anchor 150 may be released from the pusher tube 320, for example by unscrewing or otherwise detaching the distal end of the pusher tube 320 from the collar 151, as shown in FIG. 4C. The pusher tube 320 may be proximally withdrawn, exposing the drive sheath 315. The drive sheath 315 continues to retain the coupling between the drive coupler 305 and the proximal coupler 127 of the shaft 125.

Following proximal withdrawal of the pusher tube 320, the drive sheath 315 may be withdrawn as well, as shown in FIG. 4D, exposing the drive coupler 305 and the proximal coupler 127 of the drive shaft 125. As shown in FIG. 4E, once the drive coupler 305 and the proximal coupler 127 are exposed, the drive coupler 305 and, together with other components of the drive assembly 300, may be proximally withdrawn, leaving the anchoring assembly 120 at the treatment site.

Figure 5A:
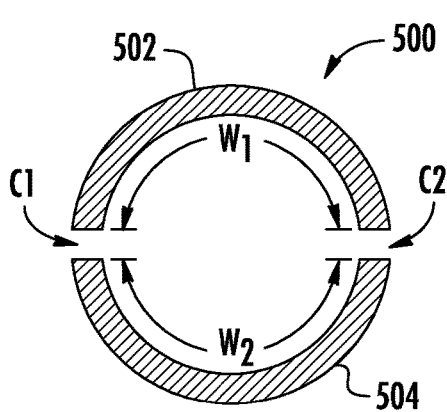
FIGS. 5A and 5B illustrate alternate embodiments of barb anchors as disclosed herein.
Figure 5B:
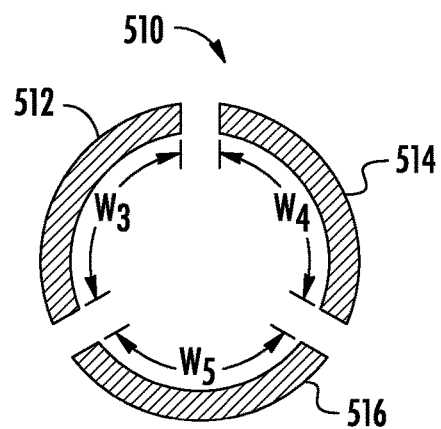

The barb anchor embodiment 150 described with regard to FIGS. 1-4E has been shown and described to include a collar and one or more arms, formed, for example, by laser cutting a hypotube. It can be appreciated, however, that a hypotube may be laser cut in a variety of manners to apportion the tube into one or more cutaway portions that may be biased in a variety of manners to form a barb anchor. For example, FIG. 5A is a cross section of a tube 500 apportioned into two cutaway portions forming arms 502, 504. The widths W1, W2 of each of the arms 502, 504 can be customized by increasing or decreasing the size of the cuts C1, C2. FIG. 5B is a cross section of a tube 510 apportioned into three cutaway portions, forming arms 512, 514, 516 of varying widths W3, W4, W5. Once apportioned, the arms 502, 504, 512, 514, 516 may be formed to be biased towards a deflected configuration as described above. Barb anchors having barb arms of increased width advantageously increases the surface area of resistance provided by the barb anchor.

Figure 6A:
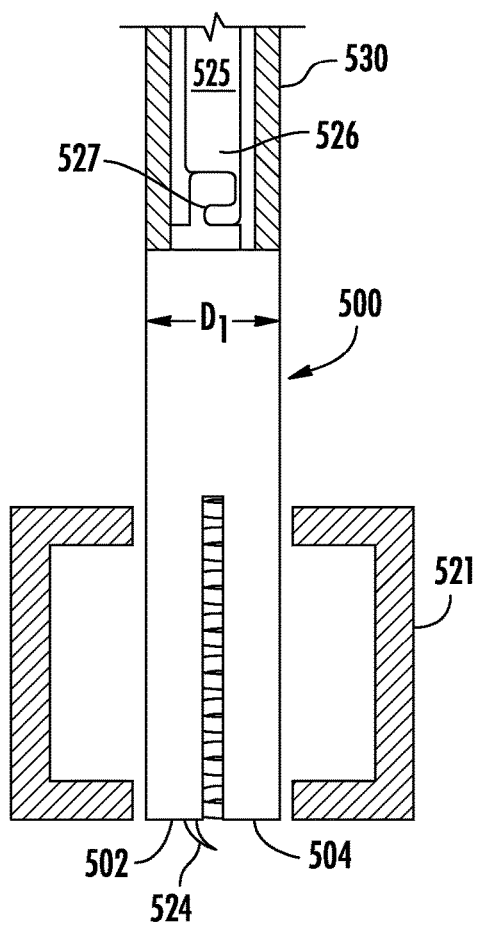
FIGS. 6A and 6B illustrate one embodiment of an anchoring assembly including the barb anchors of FIGS. 5A and 5B.

While an anchoring assembly that includes both helical anchors and barb anchors has been shown and described with regard to an embodiment where the barb anchor is a separate component from the helical anchor, it is appreciated that in various embodiments the barb anchor may be integrated with or otherwise coupled to the helical anchor. For example, a barb anchor such as barb anchor 500 of FIG. 5A, including two arms 502, 504 is shown disposed about helical anchor 524 within an anchor housing 521 in FIG. 6A. The diameter D1 of barb anchor 500 is selected to be wider than a cross section diameter of the helical anchor 524 to enable free translation of a helical anchor 524 within the barb anchor 500, for example, by actuation of a driver 525 and cooperation between a drive coupler 526 and a proximal coupler 527 of an anchor 524. A pusher tube 530 may be coupled to a proximal end of the barb anchor 500. Actuation of the helical anchor 524 by a driver 525 may distally advance the anchor 524 through the anchor housing 521.

Figure 6B:
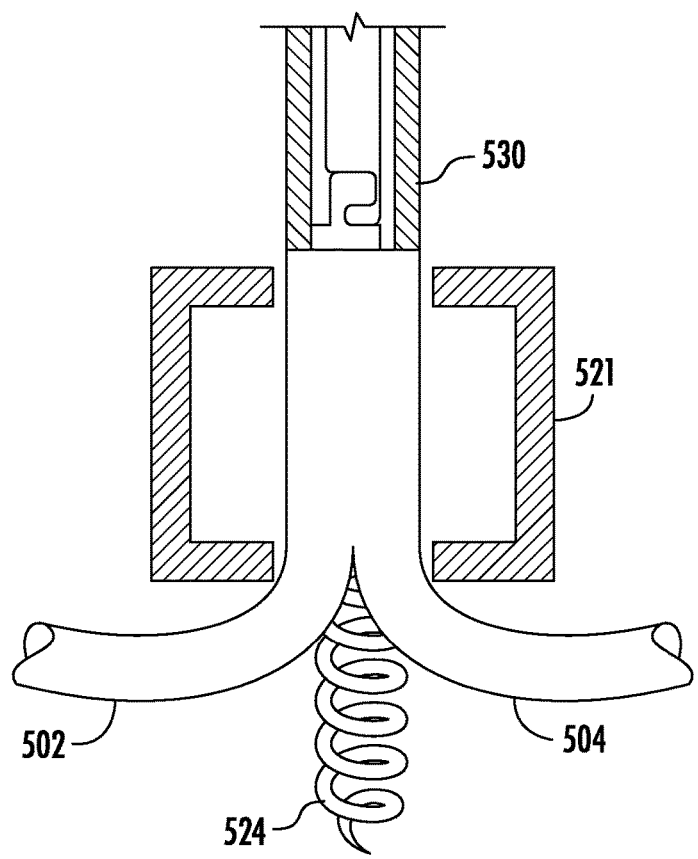

Following implantation of the helical anchor 524, as shown in FIG. 6B the pusher tube 530 may advance the barb anchor 500 into tissue, wherein the arms 502, 504 naturally assume their biased, deflected configuration.

Figure 7A:
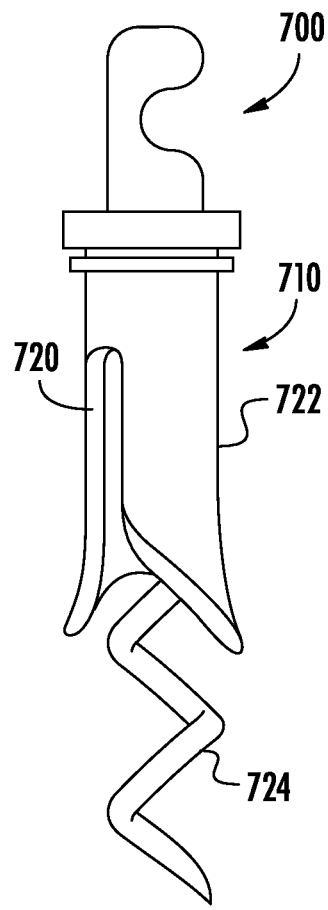
FIGS. 7A and 7B illustrate one embodiment of an anchoring assembly, where the barb anchor includes barb arms of differing lengths.
Figure 7B:
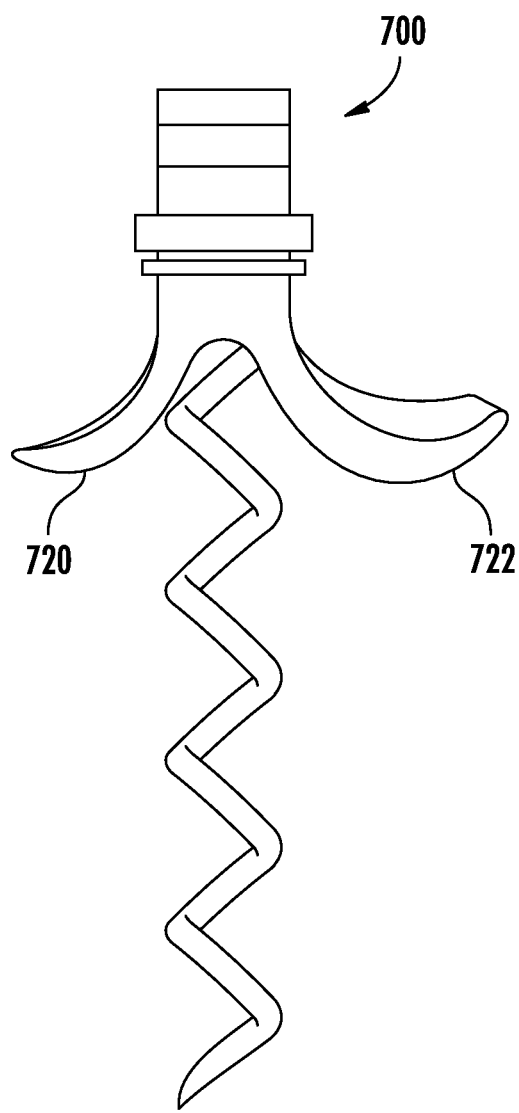

FIGS. 7A and 7B illustrate another embodiment of an anchoring assembly 700, which includes a barb anchor 710 and a helical anchor 724. In the embodiment of FIG. 7A, the barb anchor 710 is shown to be apportioned into two barb arms 720, 722, each barb arm having a different width and a different length. Barb arms 720, 722 may be advantageously cut on a bevel, for example to assist with penetration of the tissue by the relatively larger barb arm. As shown in FIG. 7B, when deployed, barb arm 722 has a greater reach and engages more tissue than barb arm 720. The anchoring assembly 700 may therefore be beneficial for tissue anchoring in regions that vary in tissue thickness or sensitivity along the anchoring surface area.

Figure 8D:
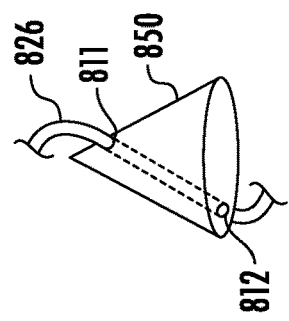
FIGS. 8A-8D illustrate one embodiment of an anchoring assembly in various stages of delivery, wherein the helical anchor includes features configured to mechanically deflect the barb anchor.

Thus far the various embodiments of barb anchors have been described to be formed of shaped memory material which automatically assumes a biased configuration based on inherent properties of the formed material. However, the present disclosure is not so limited. For example, FIGS. 8A-8C illustrate an alternate embodiment of an anchoring assembly which uses mechanical means to deflect barb arms of a barb anchor away from a central axis of the helical anchor.

Figure 8C:
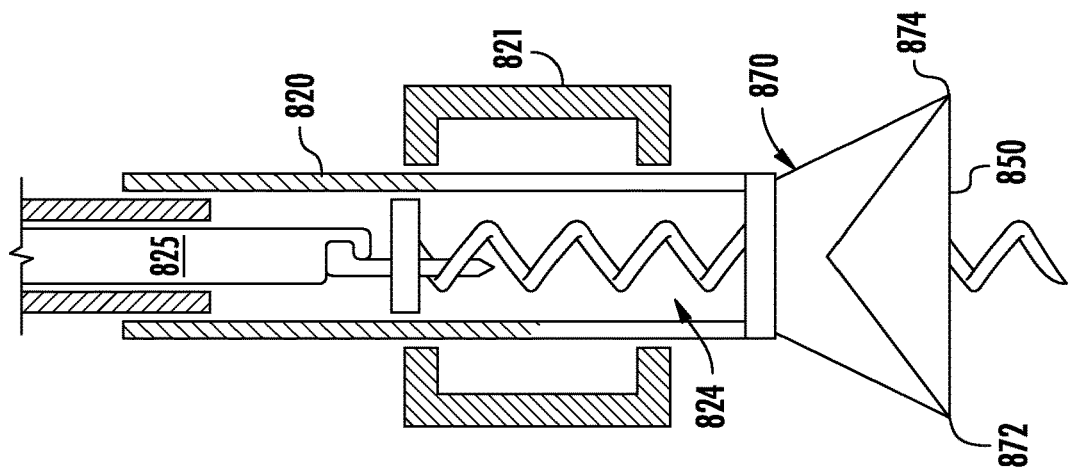
Figure 8B:
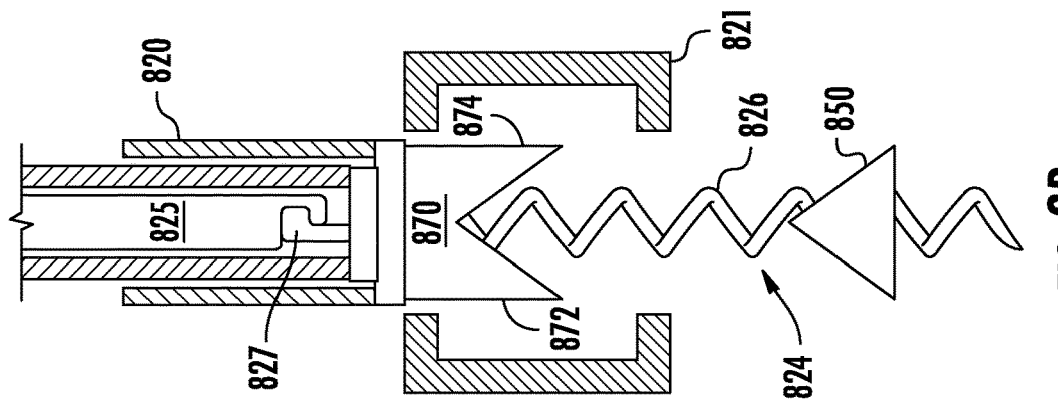
Figure 8A:
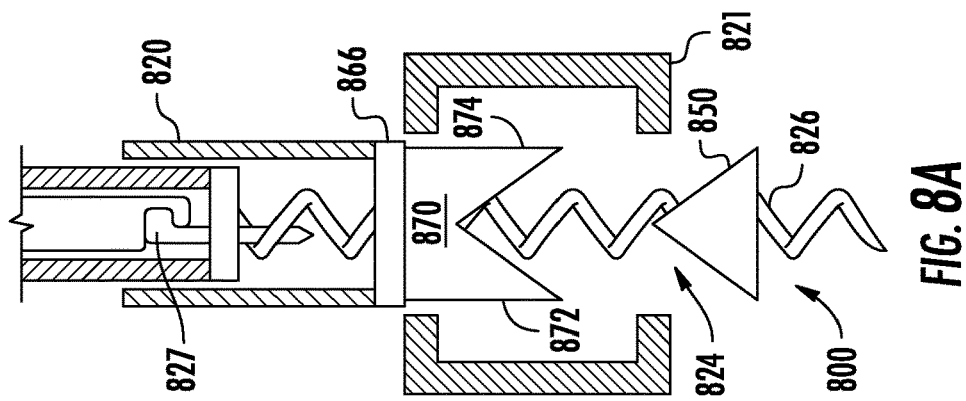

For example, FIG. 8A illustrates an anchoring system 800 within an anchor housing 821. The anchoring system 800 is shown to include a helical anchor 824 and a barb anchor 870. According to one embodiment, the barb anchor 870 may include a flange or collar 866, which is configured to mate with a distal end of the pusher arm 820, for example, via a thread, tab lock, or other method. In one embodiment, the barb anchor 870 is formed of a flexible or otherwise deformable material, such as Nitinol, stainless steel, or other polymer, and apportioned into a plurality of sharpened arms 872, 874. The helical anchor 824 includes a helical coil 826, a proximal coupler 827, and a wedge 850, fixedly disposed upon or slideably engaged with the helical coil 826 of the helical anchor 824. For example, as shown in more detail in FIG. 8D, in one embodiment the wedge 850 may be conical in shape, and have one or more opening 811, 812, through which the helical coil 826 may be threaded and/or affixed. In various embodiments, the wedge 850 may be welded, glued, or otherwise fixedly attached to the helical coil 826. The wedge may be formed of materials similar to that of the anchor 826, such as Nickel Titanium, Graphene, Nitinol, copper-aluminum-nickel, and the like. In some embodiments, the wedge may be threaded, to enable the coil to distally advance through the wedge.

According to one embodiment, the wedge 850 provides a mechanical means for spreading the barb arms 872, 874 of the barb anchor 870. For example, referring now to FIG. 8B, during deployment, the driver 825 interacts with proximal coupler 827 of the helical anchor 824 to drive the helical coil 826 into tissue. In some embodiments, the wedge 850 may be include sharpened distal edges, enabling the wedge to be advanced into tissue along with the helical coil 826. In other embodiments, the wedge is configured to allow the helical coil to thread through the wedge 850 as it is distally advanced. During actuation of the helical anchor 824, the pusher tube 820 may be maintained in a relatively proximal position, retaining at least a portion of the barb anchor 870 and respective barb arms 872, 874 within the anchor housing 821 as shown in FIG. 8B.

Referring now to FIG. 8C, once the helical anchor 824 is deployed, the pusher arm 820 may be distally advanced, pushing the barb anchor 870 through the anchor housing 821. When the barb arms 872, 874 contact the wedge 850, the wedge 850 forces apart the barb arms 872, 874, thereby increasing the resistive force acting against anchor pullout by increasing the overall surface area of the anchor. The pusher tube 820 may then be proximally withdrawn, enabling release of the driver 825 from the treatment site.

Figure 9A:
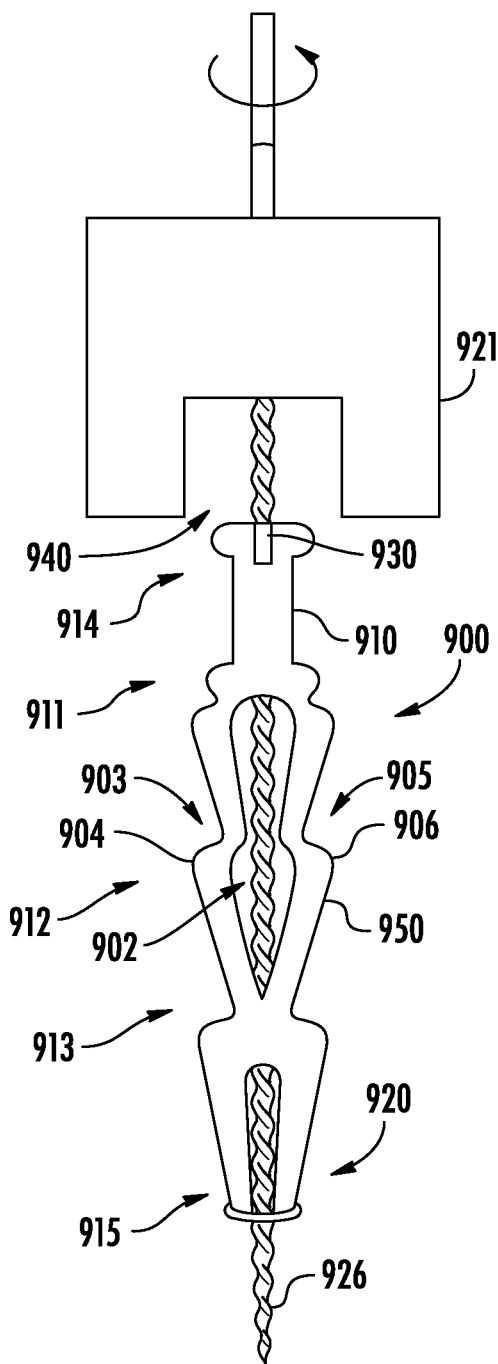
FIG. 9A-9B illustrate one embodiment of an anchoring assembly in various stages of delivery, wherein the anchoring assembly is configured for mechanical expansion of the barb anchor.
Figure 9B:
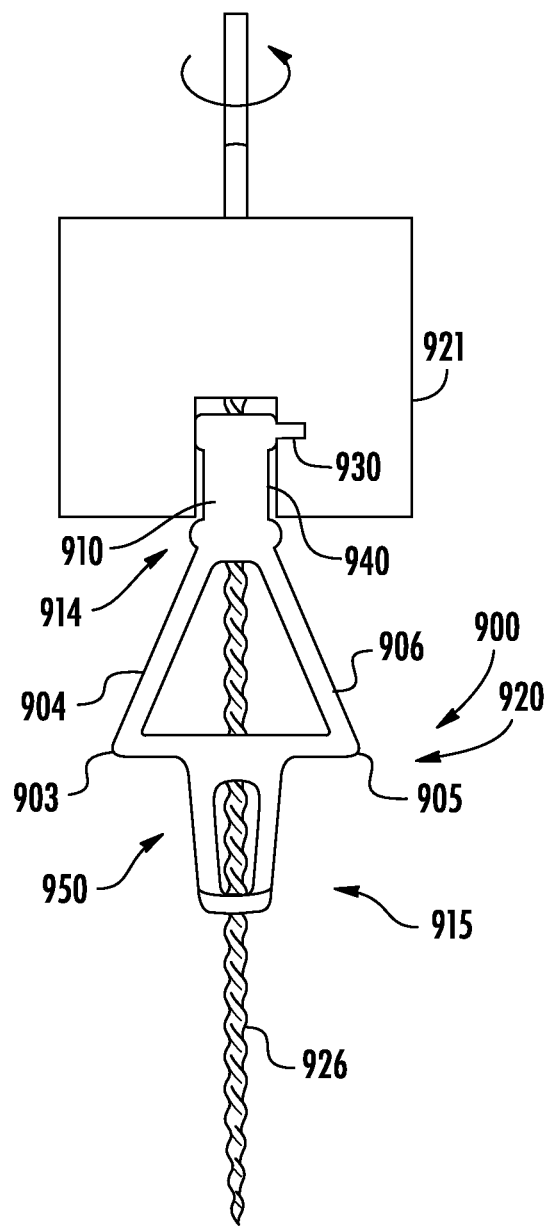

FIGS. 9A and 9B illustrate another embodiment of an anchoring system 900 including a barb anchor 950 and a helical anchor 926, for example including but not limited to a lead screw including helical threads. In one embodiment, the barbed anchor 950 comprises a proximal end 914 comprising a locking tooth 910, a distal end 915 comprising a threaded portion 920 and an elongate body disposed therebetween. In one embodiment, the elongate body is generally tubular in shape having a central lumen extending therethrough, and comprises a plurality of cutaways, such as cutaway 902, which may comprise a slit or slot that apportion the elongate body into a plurality of barb arms 904, 906. In one embodiment, each barb arm 904, 906 may be formed of a thin, flexible metal or polymer and may include one or more elbows 903, 905, wherein an elbow is a portion of the arm having increased flexibility, forming a natural bend point within the arm. In one embodiment, the barb arms comprise a generally linear configuration (shown in FIG. 9A), wherein the barb arms 904, 906 are generally aligned with the helical anchor 926, and a deflected configuration (shown in FIG. 9B), wherein the barb arms 904, 906 deflect away from the helical anchor 926, for example at the elbows 903, 905. In one embodiment, the barb arms 904, 906 may be shaped to form one or more ridges when in the linear configuration, such as ridges 911, 912, 913 of FIG. 9A. In some embodiments, the ridges, barb arm edges, external surfaces, or a combination thereof, may be sharpened or include features that enable the barb anchor 950 to cut through tissue. Thus, the ridges 911, 912, 913 may essentially function as external threads that may grab tissue as the anchor assembly 910 is driven through the anchor housing into tissue.

In one embodiment, the threaded portion 920 of the barb anchor 950 includes a thread disposed on an internal wall of the elongate body that cooperates with the threads of the anchor 926 in response to a torque force acting upon the threads to pull a distal end 915 of the barb anchor 950 towards the anchor housing 921. Generally, in the linear configuration the barb anchor 950 rotates in coordination with the anchor 926 and thus the torque force on the threaded portion 920 is minimized.

However, in one embodiment, following advancement of the anchor 926 to a desired depth, the locking tooth 910 of the barb anchor 950 may be pulled back into a coordinating slot 940 of the anchor housing 921. Such a configuration is shown in FIG. 9B. The locking tooth 910 may include external features, such as a tab 930. The tab 930 may extend radially from the locking tooth 910 and, when the locking tooth 910 is pulled into the slot 940, further rotation of the anchor 926 causes the tab 930 to contact the anchor housing 921, impeding rotation of the barb anchor 950 and generating torque force on the threaded portion of the barb anchor. It should be noted that although a tab solution is described for locking the barb anchor to the anchor housing, alternative restraint mechanisms, including coordinating threads on the external neck of the tooth and internal slot of the anchor housing and other solutions are considered within the scope of this disclosure.

Whichever method is used to lock the proximal end 914 of the barb anchor within the slot of the anchor housing 921, continued rotation of the anchor 926 exerts torque force upon the threaded portion 920, drawing the barb anchor into a deflected configuration where the distal end 915 of the barb anchor 950 is translated towards the anchor housing 921. As a result, the barb anchor 950 compresses, and the barb arms 904, 906 bend at the elbows, 903, 905, forming wings which increase the resistive surface area of the anchoring system 900 to improve anchoring integrity.

Figure 10:
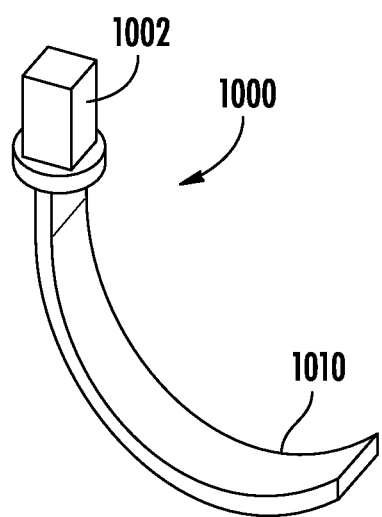
FIG. 10 illustrates one embodiment of an anchoring assembly comprising a biased ribbon anchor.

While the above described embodiments have described barb anchors which are generally tubular in shape, the present disclosure is not so limited. Rather, it is appreciated that improved anchor retention capabilities may be achieved through the use of barb anchors formed, for example from a memory-based ribbon shaped material. For example, FIG. 10 illustrates a barb anchor 1000 including a single barb arm, having a proximal coupler 1002 and an elongate body 1010 formed to be biased in a deflected configuration as shown. It is appreciated that the length, width, thickness, and deflection radius are a matter of design choice and may vary depending upon the target treatment location in which the barb anchor 1000 is to be deployed. In one example the length of the elongate body 1010 may be at least about 3 mm and at most about 12 mm, including increments of 0.1 mm therebetween. In some embodiments, the length of the elongate body may be shorter or longer than 3 mm to 12 mm in axial length, including increments of 0.1 mm therebetween. The proximal coupler 1002 and/or other non-helical portions of the anchor 1000 may be at least about 3 mm and at most about 4 mm, including increments of 0.01 mm therebetween, in axial length. In some embodiments, the proximal coupler 1002 and/or other non-helical portions may be shorter or longer than 3 mm to 4 mm in axial length, including increments of 0.01 mm therebetween.

In some embodiments, the thickness of the elongate body may be at least about 0.020 mm and at most about 2 mm, including increments of 0.1 mm therebetween. In some embodiments, the thickness may increase, decrease and/or otherwise vary along the length elongate body 1010.

In some embodiments, the width the elongate body 1010 may be at least about 0.5 mm and at most about 2 mm, including increments of 0.1 mm therebetween. In some embodiments, the width may increase, decrease or otherwise vary along the length of the elongate body 1010. In general, the width is selected to maximize the surface area contact between the anchor and neighboring tissue to secure the anchor to the tissue.

Figure 11:
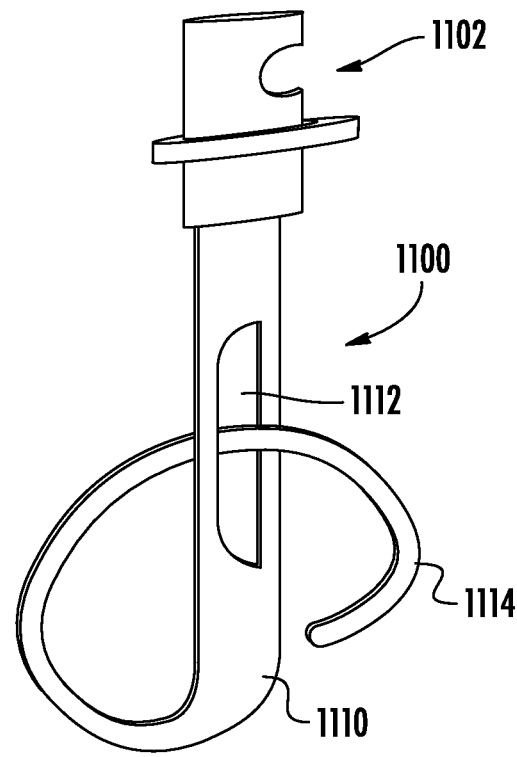
FIG. 11 illustrates one embodiment of an anchoring assembly comprising a biased ribbon anchor.

FIG. 11 illustrates a barb anchor 1100 including a proximal coupler 1102 and an elongate body 1110. In general, the barb anchor 1100 may be formed of material similar to that of the barb anchor 1000 of FIG. 10, within similar ranges of dimension. For example, the material may comprise a shape memory metal or polymer, or a pre shaped, or biased to curving material shape or composition. The elongate body 1110 is shown to include an opening 1112 extending therethrough. According to one embodiment, the deflected configuration of barb anchor 1110 is a biased looping configuration, wherein a distal tail 1114 of the elongate body 1110 may be biased to loop backwards, towards, through, or partially through the opening 1112 to capture tissue and improve anchoring integrity.

Figure 12:
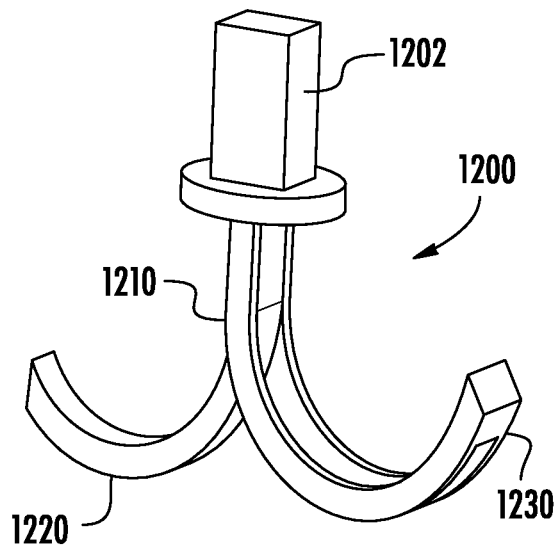
FIG. 12 illustrates one embodiment of an anchoring assembly comprising a multi-barbed biased ribbon anchor.

FIG. 12 illustrates a multi-barb anchor 1200 including a proximal coupler 1202 and an elongate body 1210 apportioned into two barb arms 1220 and 1230. In general, the multi-barb anchor 1200 may be formed of material similar to that of the barb anchor 1000 of FIG. 10, within similar ranges of dimension. In the embodiment of FIG. 12, the multi-barb anchor 1200 may be formed by laser cutting elongate body 1210 to carve out barb arm 1220. With such an arrangement, a multi-barb anchor 1200 is provided using a ribbon-based material.

Figure 13:
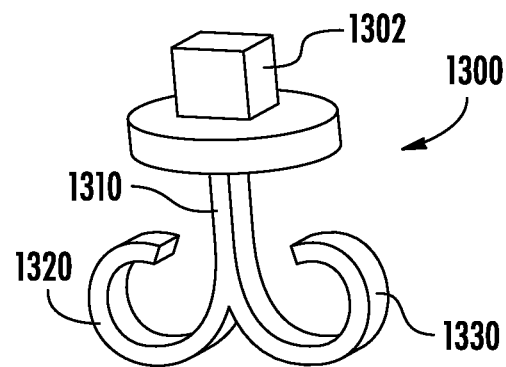
FIG. 13 illustrates one embodiment of an anchoring assembly comprising a biased multi-barbed anchor.

FIG. 12 illustrates a multi-barb anchor 1300 including a proximal coupler 1302 and an elongate body 1310 apportioned into two barb arms 1320 and 1330. In general, the multi-barb anchor 1300 may be formed of material similar to that of the barb anchor 1000 of FIG. 10, within similar ranges of dimension. In the embodiment of FIG. 13, the multi-barb anchor 1300 may be formed by bifurcating the elongate body 1310 along its thickness. In FIG. 13, the multi-bar anchor 1300 is shown having arms that loop backwards, towards the proximal coupler, enabling tissue capture within the arms and improving anchoring integrity.

Figure 14A:
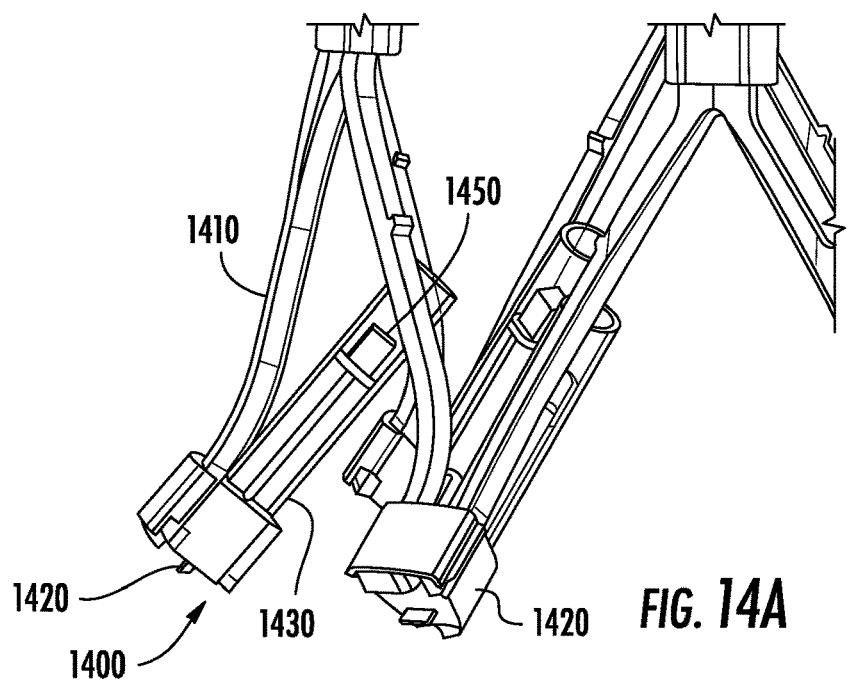
FIGS. 14A and 14B illustrate one embodiment of an anchoring assembly that may be used to deploy any of the anchors of FIGS. 10-13.
Figure 14B:
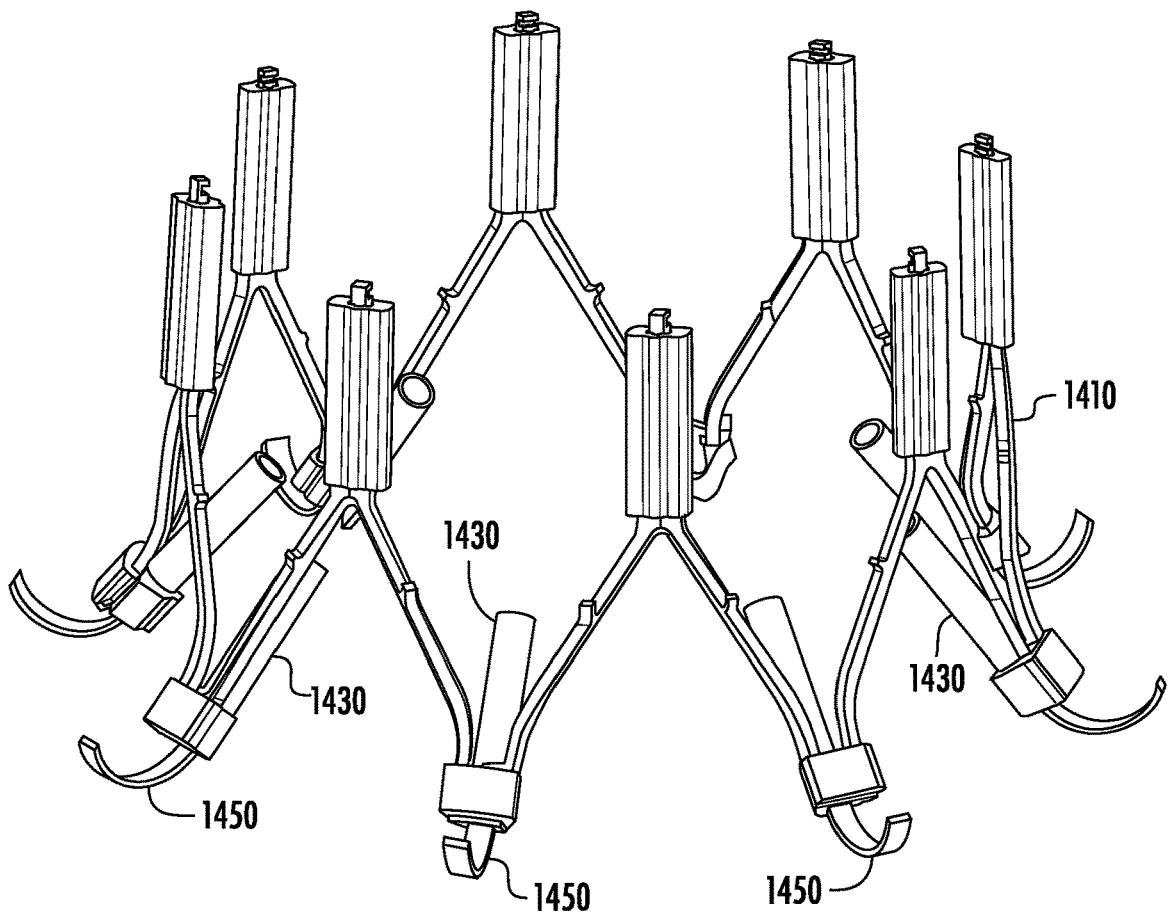

According to one embodiment, it is realized that improved anchoring integrity may be achieved using any of the barb anchors of FIGS. 10-13, or derivatives thereof in isolation (e.g., without a helical anchor). Referring now to FIG. 14A and FIG. 14B, an example of an embodiment of an anchoring assembly 1400 is shown to include a barb anchor 1450 (similar to barb anchor 1000 of FIG. 10), disposed within a barrel 1430 which may be releasably disposed within a bore of an anchor housing 1420. The barrel 1430 maintains the barb anchor 1450 in a linear configuration during delivery of the implant 1410 to the treatment site.

As shown in FIG. 14B, following delivery of the implant 1410 to the treatment site, the barb anchors 1450 may be advanced through the barrels 1430 into tissue. As the barb anchors 1450 are advanced into tissue, for example by advancing a driver (not shown) through the barrels 1430, they return to their biased, deflected configuration as illustrated in FIG. 14B. The barrels may then be withdrawn, resulting in a low profile implant solution. With such an arrangement, the amount of anchored tissue is increased, thereby improving the integrity of the anchor. Although FIG. 14B illustrates the barb anchors positioned so that the biased configuration extends generally away from the central axis of the implant 1410, it is appreciated that the barb anchors 1450 may be rotated to different orientations within the barrels, so that as the barb anchors 1450 are pushed out of the barrels, the radius of the curve of the barb anchor is differently oriented. For example, the distal ends may be oriented towards other anchor housings, or towards the central axis of the implant. In some embodiments, the driver may be configured to rotate the anchor within the barrel, enabling modifications to the orientation of the barb anchor curvature based on the particular anchoring location.

Accordingly, various embodiments of anchoring assemblies that improve anchoring integrity by increasing the surface area and/or amount of anchored tissue have been shown and described. Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. An implant configured to be disposed about a cardiac valve, the implant comprising:
   a frame;
   an anchor housing, coupled to the frame and having a bore extending therethrough and at least one barb arm sleeve offset from the bore; and
   a barb anchor, translatably disposed within the barb arm sleeve of the anchor housing, the barb anchor comprising a barb arm, the barb arm including a linear configuration wherein the barb arm is aligned with an axis of the barb arm sleeve, and a deflected configuration wherein at least a portion the barb arm is configured to deflect away from the anchor housing.

2. The implant of claim 1, wherein the barb anchor comprises a proximal end and a distal end, the proximal end comprising a collar including a coupler for connecting the barb anchor to a driver, wherein the barb arm extends distally from the collar through the opening of the anchor housing.

3. The implant of claim 1, wherein the barb arm is one of a plurality of barb arms of the barb anchor.

4. The implant of claim 3, wherein the plurality of barb arms are configured to deflect away from the central axis of the opening of the anchor housing in different deflection directions.

5. The implant of claim 4, wherein at least two of the different deflection directions are opposing directions.

6. The implant of claim 2, wherein the collar is configured for mated engagement with the driver or the anchor housing, or both.

7. The implant of claim 3, wherein at least one barb arm is formed of a material that is biased towards the deflected configuration.

8. The implant of claim 2, wherein the barb anchor comprises a neck at a proximal end and the collar comprises a flange extending radially outward from the neck, the flange having a flange diameter that is smaller than a diameter of the opening.

9. The implant of claim 1, wherein the barb sleeve is configured to retain the barb arm in the linear configuration for delivery of the implant to the cardiac valve, and the barb arm is translatable out of the barb sleeve to move into the deflected configuration.

10. The implant of claim 1, further comprising a helical anchor translatably disposed within the bore.

11. An implant delivery system including:
    a delivery catheter comprising a lumen extending therethrough;
    a drive tube extending through the lumen of the delivery catheter and having a distal end including a drive coupler;
    a pusher tube disposed about the drive tube; and
    an implant, releasably coupled to the drive tube, the implant comprising:
       a frame;
       an anchor housing coupled to the frame and having an opening extending therethrough;
       an anchor extending through a bore in the anchor housing; and
       a barb anchor, translatably disposed within an opening in the anchor housing separate from the bore, the barb anchor comprising a barb arm, the barb anchor having a linear configuration wherein the barb arm is aligned with an axis of the opening and a deflected configuration wherein at least a portion the barb arm is configured to deflect away from a central axis of the opening of the anchor housing;
    wherein:
       the drive tube is coupled to the anchor to translate the anchor through the bore; and
       the pusher tube is coupled to the barb anchor to drive the barb arm into tissue.

12. The implant delivery system of claim 11, wherein the barb anchor comprises a proximal end and a distal end, the proximal end comprising a collar including a coupler for connecting the barb anchor to the drive coupler of the drive tube, wherein the barb arm extends distally from the collar through the opening of the anchor housing in the linear configuration during delivery of the implant to a treatment site.

13. The implant delivery system of claim 11, further including a barrel, coupled to a proximal end of the opening, the barrel configured to retain the barb anchor in the linear configuration during delivery of the implant to a treatment site.

14. The implant delivery system of claim 11, wherein the barb arm is one of a plurality of barb arms of the barb anchor.

15. The implant delivery system of claim 14, wherein the plurality of barb arms are configured to deflect away from the central axis of the opening of the anchor housing in different deflection directions, at least two of the different deflection directions are opposing directions.

16. The implant delivery system of claim 11, wherein:
    the opening in the anchor housing is a barb anchor sleeve configured to retain the barb arm in the linear configuration for delivery of the implant to a location proximate to a cardiac valve and is offset from the bore extending through the anchor housing; and
    the anchor is a helical anchor translatably disposed within the bore.

17. A method of deploying an implant to a cardiac valve, of the method comprising:
    advancing a delivery catheter carrying an implant at a distal end to a treatment site proximate the cardiac valve, the implant comprising a frame including an anchor housing having at least one opening configured to translatably support a barb anchor and at least one opening configured to translatably support a helical anchor; and
    independently driving the helical anchor and the barb anchor into tissue, wherein the helical anchor and barb anchor each enter tissue at different angles relative to the anchor housing.

18. The method of claim 17, wherein:
    the opening of the anchor housing configured to translatably support a barb anchor is a barb anchor sleeve configured to retain the barb anchor in a linear configuration for delivery of the implant to the cardiac valve;
    the opening of the anchor housing configured to translatably support a helical anchor is a bore extending through the anchor housing configured for translation of the helical anchor; and
    independently driving further includes:
       driving the helical anchor through the bore of the anchor housing using a drive tube coupled to the helical anchor; and
       driving the barb anchor through the barb anchor sleeve using a pusher tube, disposed about the drive tube, the barb anchor transforming to a deflected configuration when released from the barb anchor sleeve.

19. The method of claim 17, wherein the barb anchor is disposed about the helical anchor and includes a linear configuration wherein at least one barb arm of the barb anchor is aligned with an axis of the opening configured to translatably support the barb anchor, and a deflected configuration wherein at least a portion the barb arm is configured to deflect away from the anchor housing, the method further including:
- distally translating the helical anchor through the anchor housing by actuating a drive tube coupled to the helical anchor;
- engaging a tooth of the helical anchor with a slot of the anchor housing to limit distal translation of the helical anchor through the anchor housing; and
- actuating the drive tube with the tooth of the helical anchor housing engaged with the slot of the anchor housing to translate the barb anchor from the linear configuration to the deflected configuration.

20. The method of claim 17, wherein the barb anchor is disposed about the helical anchor and includes a linear configuration wherein at least one barb arm of the barb anchor is aligned with an axis of the opening configured to translatably support the barb anchor, and a deflected configuration wherein at least a portion the barb arm is configured to deflect away from the anchor housing, and the helical anchor includes a deflection feature disposed thereon, the method further including:
- distally translating the helical anchor through the anchor housing by actuating a drive tube coupled to the helical anchor; and
- distally translating the barb anchor over the helical anchor towards the deflection feature of the helical anchor until the barb anchor is deflected away from the helical anchor by the deflection feature.

\* \* \* \* \*